(12) United States Patent
Wu et al.

(10) Patent No.: US 7,811,768 B2
(45) Date of Patent: Oct. 12, 2010

(54) MICRODEVICE CONTAINING PHOTORECOGNIZABLE CODING PATTERNS AND METHODS OF USING AND PRODUCING THE SAME

(75) Inventors: Lei Wu, San Diego, CA (US); Xiaobo Wang, San Diego, CA (US); Guoliang Tao, San Diego, CA (US); Junquan Xu, San Diego, CA (US); Jing Cheng, Beijing (CN); Mingxiang Huang, San Diego, CA (US); Baoquan Sun, Shangdong Province (CN); Wei Shao, Nanjing (CN); Litian Liu, Beijing (CN); Depu Chen, Beijing (CN); David M. Rothwarf, La Jolla, CA (US); Weiping Yang, San Diego, CA (US)

(73) Assignees: Aviva Biosciences Corporation, San Diego, CA (US); Tsinghua University, Beijing (CN); CAPTIALBIO Corporation, Beijing (CN)

( * ) Notice: Subject to any disclaimer, the term of this patent is extended or adjusted under 35 U.S.C. 154(b) by 209 days.

(21) Appl. No.: 09/924,428

(22) Filed: Aug. 7, 2001

(65) Prior Publication Data

US 2002/0137059 A1     Sep. 26, 2002

Related U.S. Application Data

(60) Provisional application No. 60/264,458, filed on Jan. 26, 2001.

(30) Foreign Application Priority Data

Feb. 23, 2001    (CN)    ................................. 01 1 04318

(51) Int. Cl.
    *G01N 33/53*    (2006.01)
(52) U.S. Cl. .............................. 435/7.1; 422/56; 422/57; 422/82.05
(58) Field of Classification Search ...................... 435/4, 435/7.1, 7.9, 287.1, 287.2; 436/146, 149, 436/151, 518, 800, 804, 805, 806, 148, 514, 436/526, 528, 801; 422/55, 57, 58, 99, 102, 422/131
    See application file for complete search history.

(56) References Cited

U.S. PATENT DOCUMENTS

| 2,797,149 | A | | 6/1957 | Skeggs |
| 3,109,719 | A | | 11/1963 | Eckert |
| 3,617,260 | A | | 11/1971 | Detert |
| 4,053,433 | A | | 10/1977 | Lee ............................. 252/408 |
| 4,390,452 | A | | 6/1983 | Stevens ................... 252/408.1 |
| 5,120,662 | A | * | 6/1992 | Chan et al. .................. 436/530 |
| 5,508,200 | A | * | 4/1996 | Tiffany et al. .................. 436/44 |
| 5,651,900 | A | | 7/1997 | Keller et al. ................... 216/56 |
| 5,660,680 | A | | 8/1997 | Keller ........................... 438/50 |
| 5,726,751 | A | | 3/1998 | Altendorf et al. |
| 5,736,330 | A | | 4/1998 | Fulton ............................. 435/6 |
| 5,858,125 | A | * | 1/1999 | Hasegawa .................... 148/304 |
| 5,893,974 | A | | 4/1999 | Keller et al. ................. 210/483 |
| 5,942,407 | A | * | 8/1999 | Liotta et al. .................... 435/28 |
| 5,981,180 | A | | 11/1999 | Chandler et al. ................ 435/6 |
| 5,998,224 | A | | 12/1999 | Rohr et al. |
| 6,029,518 | A | | 2/2000 | Oeftering .................... 73/570.5 |
| 6,048,698 | A | | 4/2000 | Eaton et al. |
| 6,057,107 | A | | 5/2000 | Fulton ............................. 435/6 |
| 6,096,496 | A | | 8/2000 | Frankel .......................... 435/4 |
| 6,114,038 | A | | 9/2000 | Castro et al. ........... 428/402.24 |
| 6,127,132 | A | | 10/2000 | Breitling et al. .............. 435/7.1 |
| 6,174,708 | B1 | | 1/2001 | Sodoyer et al. ............ 435/91.1 |
| 6,180,351 | B1 | | 1/2001 | Cattell |
| 6,214,560 | B1 | | 4/2001 | Yguerabide et al. |
| 6,221,677 | B1 | * | 4/2001 | Wu et al. ..................... 436/518 |
| 6,252,664 | B1 | | 6/2001 | Barbera-Guillem |
| 6,318,633 | B1 | * | 11/2001 | Drexler ...................... 235/454 |
| 6,355,491 | B1 | * | 3/2002 | Zhou et al. .................. 436/518 |
| 6,361,749 | B1 | | 3/2002 | Terstappen et al. |
| 6,492,125 | B2 | * | 12/2002 | Kauvar et al. ................ 435/7.1 |
| 6,548,264 | B1 | | 4/2003 | Tan et al. |
| 7,015,047 | B2 | | 3/2006 | Huang et al. |
| 7,262,016 | B2 | | 8/2007 | Huang et al. |
| 2002/0022276 | A1 | | 2/2002 | Zhou et al. |
| 2002/0034042 | A1 | * | 3/2002 | Hungerford et al. ......... 360/121 |

(Continued)

FOREIGN PATENT DOCUMENTS

EP          0629989          12/1994

(Continued)

OTHER PUBLICATIONS

Finucane et al. Biochemistry 1999 vol. 38, p. 11604-11612.*

(Continued)

*Primary Examiner*—Jacob Cheu
(74) *Attorney, Agent, or Firm*—Morrison & Foerster LLP

(57) ABSTRACT

This invention relates generally to the field of moiety or molecule analysis, isolation, detection and manipulation and library synthesis. In particular, the invention provides a microdevice, which microdevice comprises: a) a substrate; and b) a photorecognizable coding pattern on the substrate. Preferably, the microdevice does not comprise an anodized metal surface layer. Methods and kits for isolating, detecting and manipulating moieties, and synthesizing libraries using the microdevices are also provided. The invention further provides two-dimensional optical encoders and uses thereof.

24 Claims, 11 Drawing Sheets

U.S. PATENT DOCUMENTS

| | | |
|---|---|---|
| 2002/0187501 A1 | 12/2002 | Huang et al. |
| 2006/0024732 A1 | 2/2006 | Huang et al. |

FOREIGN PATENT DOCUMENTS

| | | | |
|---|---|---|---|
| GB | 1568699 | | 6/1980 |
| GB | 2306484 | * | 10/1995 |
| GB | 2289150 | | 11/1995 |
| GB | 2306484 | | 5/1997 |
| WO | WO 96/39937 | | 12/1996 |
| WO | WO-97/32892 | | 9/1997 |
| WO | WO-97/40385 | | 10/1997 |
| WO | WO 99/47254 | | 9/1999 |
| WO | WO 00/16893 | * | 3/2000 |
| WO | WO 00/16893 | | 5/2000 |
| WO | WO 00/54882 | | 9/2000 |
| WO | WO-01/25002 | | 4/2001 |
| WO | WO-01/78889 | | 10/2001 |
| WO | WO-02/27909 | | 4/2002 |
| WO | WO-02/31505 | | 4/2002 |
| WO | WO-02/33419 | | 4/2002 |

OTHER PUBLICATIONS

Villeneuve et al. J. Pharmacology & Toxicological Method 1998 vol. 40, p. 95-100.*
U.S. Appl. No. 09/636,104, filed Aug. 10, 2000, Wang et al.
U.S. Appl. No. 09/679,024, filed Oct. 4, 2000, Wang et al.
Ahn et al., J. of Microelectromechanical Systems (1996) 5:151-157.
Ashkin, Biophys. J. (1992) 61:569-582.
Bart et al., Sensors and Acuators (1988) 14:269-292.
Becker et al., Proc. Natl. Acad. Sci. (1995) 92:860-864.
Block, Nature (1992) 360:493-496.
Chu, Science (1991) 253:861-866.
Dolle, Journal of Combinatorial Chemistry (2000) 2:383-433.
Fuhr et al., Sensors and Materials (year?) 7:131-146.
Hagedorn et al., Journal of Electrostatics (1994) 33:159-185.
Huang et al., J. Phys. D.: Appl. Phys. (1993) 26:1528-1535.
Kronick, in Methods of Cell Separation, vol. 3, Catsimpoolas (ed.) (1980) pp. 115-139.
Oliver et al., Clinical Chemistry (1998) 44:2057-2060.
Safarik and Safarikova, J. of Chromatography (1999) 722(B):33-53.
Vignali, J. Immunol. Methods (2000) 243:243-255.
Wang et al., Biochim. Biophys. Acta (1995) 1243:185-194.
Wang et al., Biophys. J. (1997) 72:1887-1899.
Wang et al., IEEE Transaction on Industry Applications (1997) 33(3):660-669.
Wang et al., Science (1998) 280:1077-1082.
Wright et al., IEEE J. of Quantum Electronics (1990) 26:2148-2157.
Yasuda et al., Jpn. J. Appl. Physics (1996) 35:3295-3299.
Yoshioka and Kawashima, Acustica (1995) 5:167-173.
Anonymous, "Light-Emitting Chips Speed Up Drug Discovery" Chemical Engineering 107(10):23 (2000).
Terrett, N., "Encoded Combinatorial Synthesis" Chapter 5 In Combinatorial Chemistry Oxford University Press pp. 46-94 (1998).
Blanchard et al., Biosensors Bioelectronics (1996) 6/7:687-690.
Bleaney and Bleaney, Electricity and Magnetism, Oxford, 1975, pp. 169-174, 519-524.
Bruchez et al., Science (1998) 281:2013-2015.
Chan and Nie, Science (1998) 281:2016-2018.
Ferguson et al., Anal. Chem. (2000) 72:5618-5624.
Fodor et al., Science (1991) 251:767-773.
Han et al, Nature Biotechnology (2001) 19:631-635.
Lam et al., Chem. Rev. (1997) 97:411-448.
Mc Gall et al., J. Am. Chem. Soc. (1997) 119:5081-5090.
Nicewarner-Pena et al., Science (2001) 294(5540):137-141.
Schena et al., Science (1995) 270:467-470.
Singh-Gasson et al., Nature Biotechnology (1999) 17:974-978.
Zammatteo et al., Anal. Biochem. (2000) 280:143-150.
U.S. Appl. No. 11/841,935, filed Aug. 20, 2007.
U.S. Appl. No. 11/230,411, filed Sep. 20, 2005.
Non-Final Office Action for U.S. Appl. No. 11/230,411, date mailed on Jun. 2, 2006.
Amendment in Response to Non-Final Office Action for U.S. Appl. No. 11/230,411, filed Sep. 5, 2006.
Non-Final Office Action for U.S. Appl. No. 11/230,411, date mailed on Nov. 28, 2006.
Amendment in Response to Non-Final Office Action for U.S. Appl. No. 11/230,411, filed on Sep. 27, 2007.
Notice of Non-Compliant Amendment for U.S. Appl. No. 11/230,411, date mailed on Mar. 15, 2007.
Amendment in Response to Non-Final Office Action for U.S. Appl. No. 11/230,411, filed on Mar. 21, 2007.
Notice of Allowance for U.S. Appl. No. 11/230,411, date mailed on Mar. 27, 2007.
Substance of Examiner Interview for U.S. Appl. No. 11/230,411, filed on Apr. 20, 2007.
U.S. Appl. No. 10/104,571, filed Mar. 21, 2002.
Non-Final Office Action for U.S. Appl. No. 10/104,571, date mailed on Mar. 25, 2004.
Amendment and Response under 37 C.F.R. 1.111 for U.S. Appl. No. 10/104,571, filed Jul. 23, 2004.
Non-Final Office Action for U.S. Appl. No. 10/104,571, date mailed on Oct. 19, 2004.
Amendment in Response to Non-Final Office Action for U.S. Appl. No. 10/104,571, filed Jan. 14, 2005.
Notice of Non-Compliant Amendment for U.S. Appl. No. 10/104,571, date mailed on Feb. 4, 2005.
Response to Notice of Non-Compliant Amendment for U.S. Appl. No. 10/104,571, filed on Mar. 4, 2005.
Notice of Allowance for U.S. Appl. No. 10/104,571, date mailed on Jun. 15, 2005.
Statement of Substance of Interview for U.S. Appl. No. 10/104,571, filed on Jul. 7, 2005.
Corrected Notice of Allowance for U.S. Appl. No. 10/104,571, date mailed on Oct. 13, 2005.
Amendment under 37 C.F.R. 1.312 for U.S. Appl. No. 10/104,571, filed on Nov. 8, 2005.
Petition to Withdraw Application from Issue Pursuant to 37 C.F.R. 1.313(c)(3) for U.S. Appl. No. 10/104,571, filed Nov. 8, 2005.
Response to Rule 312 Communication, date mailed on Jan. 26, 2006.
Non-Final Office Action U.S. Appl. No. 11/841,935, mailed on Apr. 1, 2009, 18 pages.
International Search Report for PCT/US03/07468 mailed on Sep. 20, 2004, 5 pages.
Supplementary European Search Report for EP 03 74 5098, mailed on Jun. 18, 2010, 5 pages.

* cited by examiner

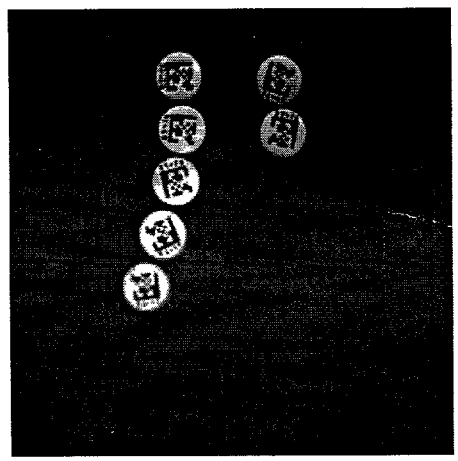
FIG. 9
FIG. 10A
FIG. 10B
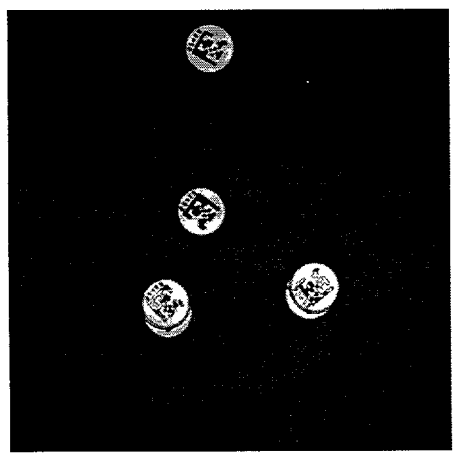
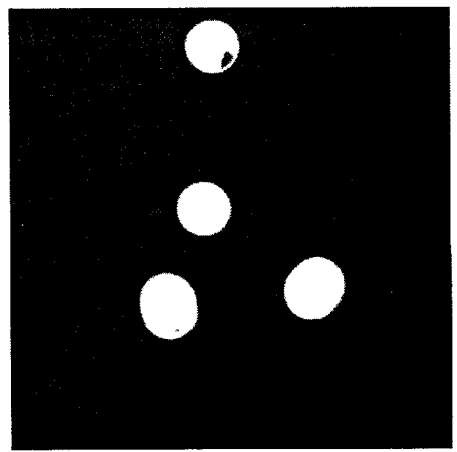
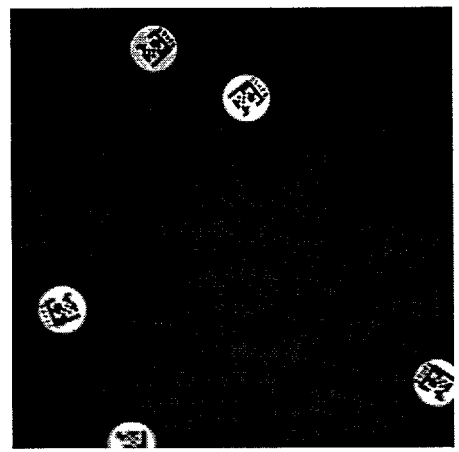
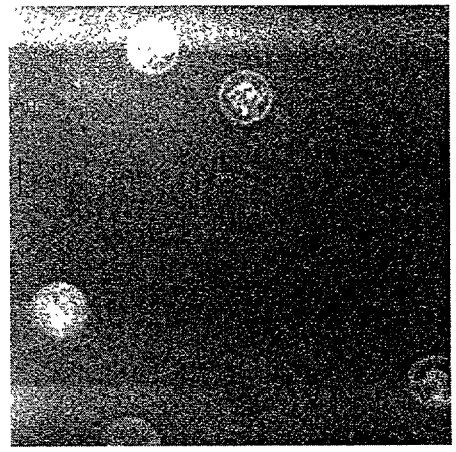
FIG. 10C
FIG. 10D FIG. 11A
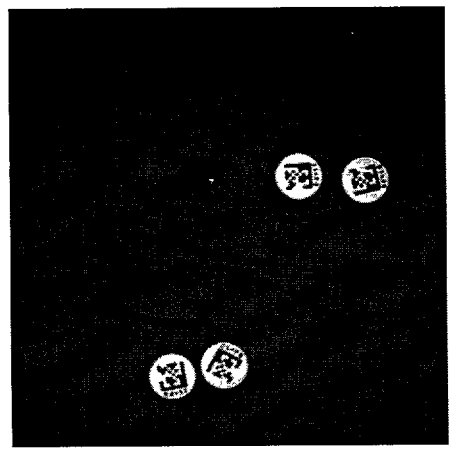
FIG. 11B
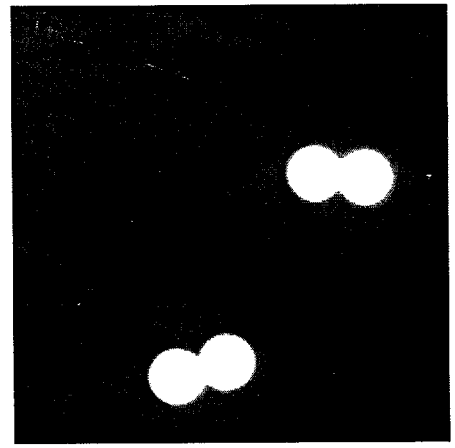
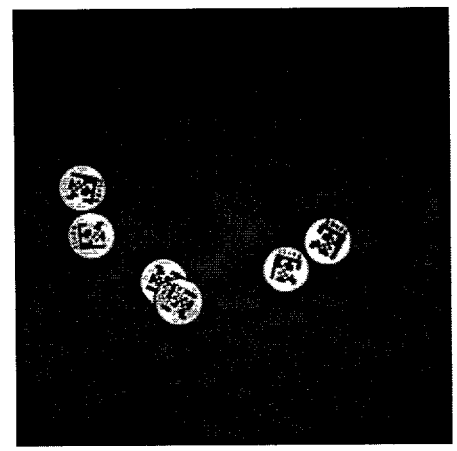
FIG. 11C
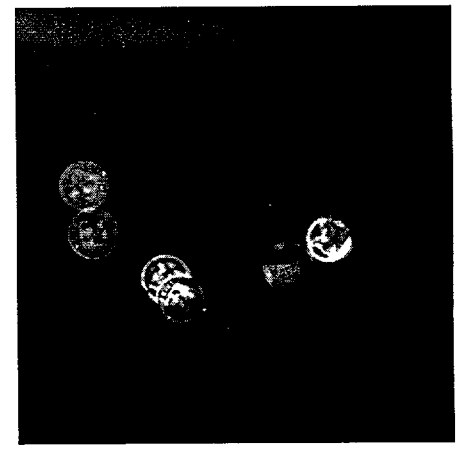
FIG. 11D
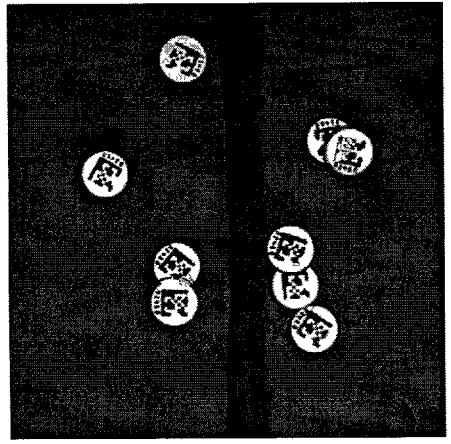
FIG. 12A
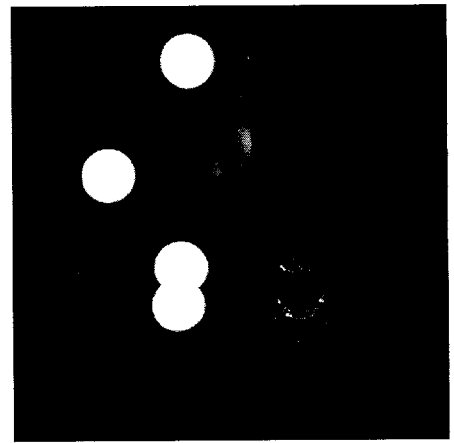
FIG. 12B FIG. 13
FIG. 13A
FIG. 13B
FIG. 13C
FIG. 13D
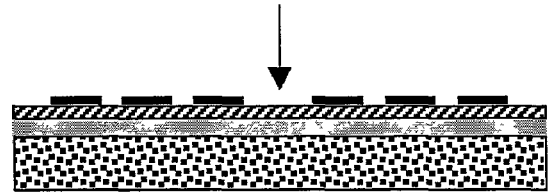
FIG. 13E
FIG. 13F
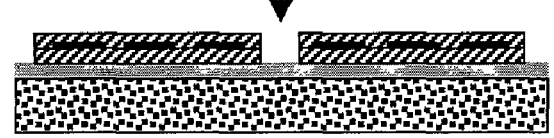
FIG. 13G
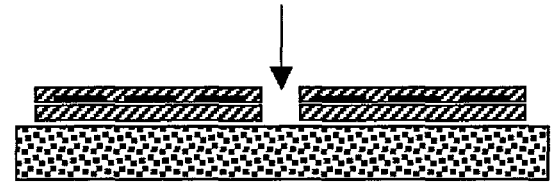
FIG. 13H (A)

(B)

(C)

MICRODEVICE CONTAINING PHOTORECOGNIZABLE CODING PATTERNS AND METHODS OF USING AND PRODUCING THE SAME

This application claims priority benefit of U.S. Provisional Patent Application Ser. No. 60/264,458, filed Jan. 26, 2001 under 35 U.S.C. §119(e) and Chinese Patent Application Serial No. 01104318.0, filed Feb. 28, 2001 under 35 U.S.C. §119(a)-(d). The disclosures of the above applications are incorporated herein by reference in their entireties.

TECHNICAL FIELD

This invention relates generally to the field of moiety or molecule analysis, isolation, detection, analysis, manipulation and chemical synthesis. In particular, the invention provides a microdevice, which microdevice comprises: a) a substrate; and b) a photorecognizable coding pattern on said substrate. Preferably, the microdevice does not comprise an anodized metal surface layer. Methods and kits for isolating, detecting, analyzing and manipulating moieties, and synthesizing compounds or libraries using the microdevices are also provided. The invention further provides two-dimensional optical encoders and uses thereof.

BACKGROUND ART

Micro array technology has revolutionized the biotechnology industry. Its ability to process large number of biological samples in parallel is unprecedented. The current micro array technologies can be generally categorized into two groups. One group is based on a two-dimensional solid support system, on which all the biological reactions and signal detections are completed (see e.g., "Large-scale identification, mapping and genotyping of single-nucleotide polymorphisms in the human genome" by Wang, D. G., et al., Science, Volume 280: pages 1077-1082 (1998)). The other group utilizes microparticles as reaction platform. One example of such technology is the fluorescent particle technology or three-dimensional micro array (see e.g. "Multiplexed particle-based flow cytometric assays" by Vignali, D A., J. Immunol. Methods, Volume 243, pages 243-255 (2000); "Multiplexed analysis of human cytokines by use of the Flow-Metrix system" by Oliver K G, et al., *Clinical Chemistry* Volume 44, Pages 2057-2060 (1998); and U.S. Pat. Nos. 6,057,107, 5,981,180 and 5,736,330). Limitations have been observed on both types of technologies. Biological reaction conducted on the two-dimensional based technology platform is limited by molecule diffusion. In general, a longer reaction time is required for the two-dimensional reaction platforms. The three-dimensional fluorescence particle technology has problems in the complexity of the technology and limitation on numbers of particle encoding, e.g., only hundreds or thousands of encoding are available. In addition, the detection of two-color fluorescence levels on the microparticles requires sophisticated instrumentation.

WO 00/16893 discloses a system for carrying out parallel bioassays. Microfabricated labels are made to each carry a biochemical test, many different labels are mixed together with an analyte sample. A device that reads the individual labels isolates the results of the individual tests. The microfabricated labels have a surface layer of anodized metal and are produced by anodizing, lithographic patterning and etching steps. Aluminum is the preferred metal.

In modern pharmaceutical industry, a very important approach for developing new drugs is through the screening of combinatorially synthesized compound libraries. Combinatorial chemistry is high-throughput, rapid and "synchronized" method that can synthesize the structurally-similar compounds and derivatives of a lead compound. While previous synthesis methods are primarily based on individual compound synthesis, combinatorial chemistry is capable of synthesizing thousands to tens of thousands compounds in serial and parallel fashions (Dolle, *Journal of Combinatorial Chemistry*, 2:383-433 (2000)).

DISCLOSURE OF THE INVENTION

In one aspect, the present invention is directed to a microdevice, which microdevice comprises: a) a substrate; and b) a photorecognizable coding pattern on said substrate. Preferably, the microdevice does not comprise an anodized metal surface layer, e.g., an anodized aluminium surface layer.

In another aspect, the present invention is directed to a method for isolating a moiety, which method comprises: a) providing a microdevice comprising a substrate, a photorecognizable coding pattern on said substrate and a binding partner that is capable of binding to a moiety to be isolated; b) contacting a sample containing or suspected of containing said moiety with said microdevice provided in step a) under conditions allowing binding between said moiety and said binding partner; and c) recovering said microdevice from said sample, whereby the identity of said isolated moiety is assessed by photoanalysis (or optical analysis) of said photorecognizable coding pattern. Preferably, the microdevice used in the method does not comprise an anodized metal surface layer, e.g., an anodized aluminium surface layer.

In still another aspect, the present invention is directed to a method for isolating a plurality of moieties, which method comprises: a) providing a plurality of microdevices each comprising a substrate, a photorecognizable coding pattern on said substrate and a binding partner that is capable of binding to one type of moieties to be isolated; b) contacting a sample containing or suspected of containing said moieties with said microdevice provided in step a) under conditions allowing binding between said moieties and their corresponding binding partners; and c) recovering a plurality of microdevices from said sample, whereby the identity of said isolated moiety is assessed by photoanalysis (or optical analysis) of said photorecognizable coding pattern. Preferably, at least one of the microdevices used in the method does not comprise an anodized metal surface layer, e.g., an anodized aluminium surface layer. More preferably, at least 50% or all of the microdevices used in the method do not comprise an anodized metal surface layer, e.g., an anodized aluminium surface layer.

In yet another aspect, the present invention is directed to a method for manipulating a moiety, e.g., in a microfluidic application, which method comprises: a) providing a microdevice comprising a substrate, a photorecognizable coding pattern on said substrate and a binding partner that is capable of binding to a moiety to be manipulated; b) coupling said moiety to said microdevice provided in step a) via binding between said moiety and said binding partner to form a moiety-microdevice complex; and c) manipulating said moiety-microdevice complex with a physical force, preferably in a chip format, thereby said moiety is manipulated. The above method for manipulating a moiety can be readily extended to manipulating multiple moieties by using multiple microdevices, each of which is targeted to one type of moieties to be manipulated. Preferably, the microdevice used in the method does not comprise an anodized metal surface layer, e.g., an anodized aluminium surface layer.

In yet another aspect, the present invention is directed to a kit for manipulating a moiety, e.g. in a microfluidic application, which kit comprises: a) a microdevice comprising a substrate, a photorecognizable coding pattern on said substrate and a binding partner that is capable of binding to a moiety to be manipulated; and b) a chip on which a moiety-microdevice complex can be manipulated. Preferably, the microdevice used in the kit does not comprise an anodized metal surface layer, e.g., an anodized aluminium surface layer.

In yet another aspect, the present invention is directed to a method for detecting a moiety, which method comprises: a) providing a microdevice comprising a substrate, a photorecognizable coding pattern on said substrate and a binding partner that is capable of binding to a moiety to be detected; b) contacting a sample containing or suspected of containing said moiety with said microdevice provided in step a) under conditions allowing binding between said moiety and said binding partner; and c) detecting binding between said moiety and said binding partner, whereby the presence or amount of said moiety is assessed by analysis of binding between said moiety and said binding partner and the identity of said moiety is assessed by photoanalysis (or optical analysis) of said photorecognizable coding pattern. Preferably, the microdevice used in the method does not comprise an anodized metal surface layer, e.g., an anodized aluminium surface layer. The above method for detecting a moiety can be readily extended to detecting multiple moieties by using multiple microdevices, each of which is targeted to one type of moieties to be manipulated.

In yet another aspect, the present invention is directed to an array of microdevices for detecting moieties, which array comprises a plurality of microdevices located, positioned or immobilized on a surface, e.g., a chip, each of said microdevices comprises a photorecognizable coding pattern on a substrate and a binding partner that is capable of binding to a moiety to be detected. Preferably, at least one of the microdevices used in the array does not comprise an anodized metal surface layer, e.g., an anodized aluminium surface layer. More preferably, at least 50% or all of the microdevices used in the array do not comprise an anodized metal surface layer, e.g., an anodized aluminium surface layer.

In yet another aspect, the present invention is directed to a method for synthesizing a library, which method comprises: a) providing a plurality of microdevices, each of said microdevices comprises a substrate and a photorecognizable coding pattern on said substrate, wherein said photorecognizable coding pattern corresponds to an entity to be synthesized on said microdevice; and b) synthesizing said entities on said microdevices, wherein said microdevices are sorted after each synthesis cycle according to said photorecognizable coding patterns, whereby a library is synthesized, wherein each of said microdevices contains an entity that corresponds to a photorecognizable coding pattern on said microdevice and the sum of said microdevices collectively contains a plurality of entities that is predetermined before the library synthesis. Preferably, at least one of the microdevices used in the method does not comprise an anodized metal surface layer, e.g., an anodized aluminium surface layer. More preferably, at least 50% or all of the microdevices used in the method do not comprise an anodized metal surface layer, e.g., an anodized aluminium surface layer.

In yet another aspect, the present invention is directed to a method for generating an antibody library, which method comprises: a) contacting a library synthesized by the above-described method with a plurality of antibodies; and b) selecting and/or recovering antibodies that specifically bind to the entities of the library synthesized by the above-described method. Preferably, at least one of the microdevices used in the method does not comprise an anodized metal surface layer, e.g., an anodized aluminium surface layer. More preferably, at least 50% or all of the microdevices used in the method do not comprise an anodized metal surface layer, e.g., an anodized aluminium surface layer.

In yet another aspect, the present invention is directed to a two-dimensional optical encoder, which encoder comprises: a) a substrate; and b) a microfabricated or micromachined two-dimensional optical code on said substrate. Preferably, the two-dimensional optical encoder does not comprise an anodized metal surface layer, e.g., an anodized aluminium surface layer.

BRIEF DESCRIPTION OF THE DRAWINGS

FIG. 9 shows orientation of MicroDisks following magnetic manipulation.

FIG. 10 shows results of a covalent attachment experiment.

FIG. 11 shows results of a bioassay experiment.

FIG. 12 shows further results of a bioassay experiment determining the amount of fluorescence signal from both types of MicroDisks in the same measurement.

FIG. 13 shows an exemplary fabrication process for making one type of microdevices (or encoding particles) of the present invention.

FIG. 13A shows preparation of the substrate;
FIG. 13B shows deposition of the sacrificial layer;
FIG. 13C shows deposition of the first layer;
FIG. 13D shows deposition of the second layer;
FIG. 13E shows patterning of the second layer;
FIG. 13F shows deposition of the third layer;
FIG. 13G shows patterning of the first and the third layers; and
FIG. 13H shows etching of the sacrificial layer.

MODES FOR CARRYING OUT THE INVENTION

Figure 1:
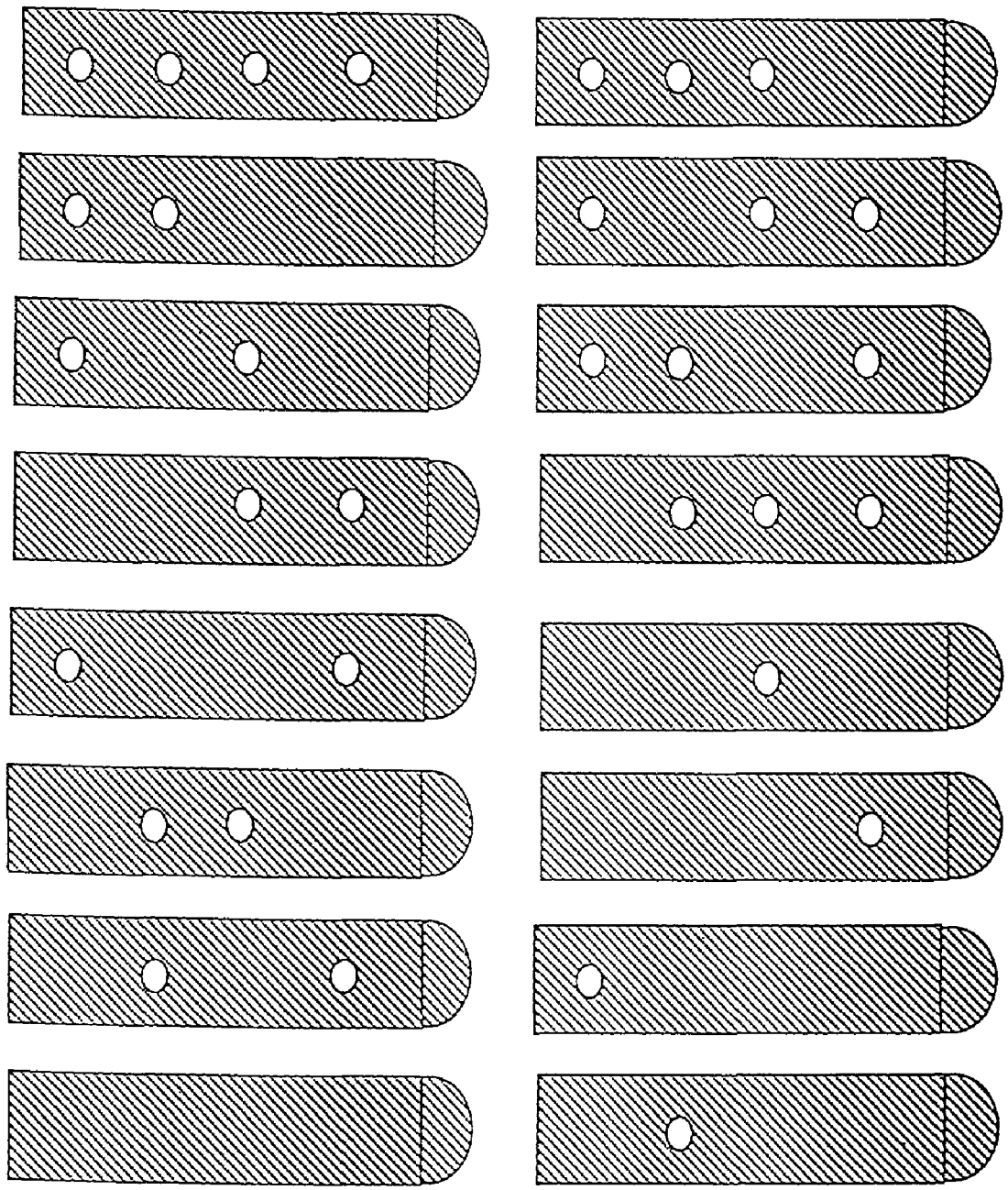
FIG. 1 illustrates encoding examples of microdevices (microstructures) wherein the microdevices are in rectangular shape and the holes are introduced along the middle lines of the structures.

For clarity of disclosure, and not by way of limitation, the detailed description of the invention is divided into the subsections that follow.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this section prevails over the definition that is incorporated herein by reference.

As used herein, "a" or "an" means "at least one" or "one or more."

As used herein, "a photorecognizable coding pattern" refers to any coding pattern that can be detected and/or assessed by photoanalysis (optical analysis). Any photorecognizable property can be used as the characteristics of the coding pattern. For example, the photorecognizable coding pattern can be the material composition of the substrate itself, a hole in the substrate or a substance immobilized on the substrate, said substance having an optical refractive property that is different from the optical refractive property of the substrate. The versatility of the photorecognizable coding pattern can be based on the shape, number, position distribution, optical refractive property, material composition, or a combination thereof, of the substrate, the hole(s), or the substance(s) located, deposited or immobilized on the substrate. To facilitate optical analysis (or photoanalysis) of encoding patterns, certain microdevices may incorporate "orientation" marks or alignment markers. For example, for the microdevices having thin circular disk shapes, the microdevices lying flat on either of its major surfaces will look identical, causing difficulties in identification. Therefore, the orientation markers can be used for indicating which major surface is up and for helping decode the patterns.

As used herein, "a photorecognizable coding pattern on said substrate" means that the photorecognizable coding pattern is located on, in, or within (or inside) the substrate so that the photorecognizable coding pattern is optically detectable. For example, the photorecognizable coding pattern can be located on the surface or on top of the substrate. The photorecognizable coding pattern can also be located within or inside the substrate. In other embodiments, the substrate may have multiple layers and the photorecognizable coding pattern can be located on the surface layer, on top of the surface layer, or can be located within or inside one or more layers.

As used herein, "the photorecognizable coding pattern is fabricated or microfabricated on the substrate" means the use of any microfabrication or micromachining methods to produce or generate encoding patterns on the substrate. Various semiconductor fabrication protocols such as, pattern masking, photolithography, wet etching, reactive-ion-etching and deep-reactive-ion-etching, etc., can be used.

As used herein, "chip" refers to a solid substrate with a plurality of one-, two- or three-dimensional micro structures or micro-scale structures on which certain processes, such as physical, chemical, biological, biophysical or biochemical processes, etc., can be carried out. The micro structures or micro-scale structures such as, channels and wells, electrode elements, electromagnetic elements, are incorporated into, fabricated on or otherwise attached to the substrate for facilitating physical, biophysical, biological, biochemical, chemical reactions or processes on the chip. The chip may be thin in one dimension and may have various shapes in other dimensions, for example, a rectangle, a circle, an ellipse, or other irregular shapes. The size of the major surface of chips of the present invention can vary considerably, e.g., from about 1 $mm^2$ to about 0.25 $m^2$. Preferably, the size of the chips is from about 4 $mm^2$ to about 25 $cm^2$ with a characteristic dimension from about 1 mm to about 5 cm. The chip surfaces may be flat, or not flat. The chips with non-flat surfaces may include channels or wells fabricated on the surfaces.

As used herein, "physical field," e.g., used itself or used as "physical field in a region of space" or "physical field is generated in a region of space" means that the region of space has the following characteristics. When a moiety, alone or bound to a microdevice via a binding partner, of appropriate properties is introduced into the region of space (i.e. into the physical field), forces are produced on the moiety, the microdevice or both, as a result of the interaction between the moiety and/or microdevice and the field. A moiety can be manipulated within a field via the physical forces exerted on the moiety by the field. Exemplary fields include electric, magnetic, acoustic, optical and velocity fields. In the present invention, physical field always exists in a medium in a region of space, and the moiety to be manipulated is suspended in, or is dissolved in, or more generally, is placed in the medium. Typically, the medium is a fluid such as aqueous or non-aqueous liquids, or a gas. Depending on the field configuration, an electric field may produce electrophoretic forces on charged moieties, or may produce conventional dielectrophoretic forces and/or traveling wave dielectrophoretic forces on charged and/or neutral moieties. Magnetic field may produce magnetic forces on magnetic moieties. Acoustic field may produce acoustic radiation forces on moieties. Optical field may produce optical radiation forces on moieties. Velocity field in the medium in a region of space refers to a velocity distribution of the medium that moves in the region of the space. Various mechanisms may be responsible for causing the medium to move and the medium at different positions may exhibit different velocities, thus generating a velocity field. Velocity field may exert mechanical forces on moieties in the medium.

As used herein, "medium (or media)" refers to a fluidic carrier, e.g., liquid or gas, wherein a moiety, alone or bound to a microdevice via a binding partner, is dissolved, suspended or contained.

As used herein, "microfluidic application" refers to the use of microscale devices, e.g., the characteristic dimension of basic structural elements is in the range between less than 1 micron to 1 cm scale, for fluidic manipulation and process, typically for performing specific biological, biochemical or chemical reactions and procedures. The specific areas include, but are not limited to, biochips, i.e., chips for biologically related reactions and processes, chemchips, i.e., chips for chemical reactions, or a combination thereof. The characteristic dimensions of the basic elements refer to the single dimension sizes. For example, for the microscale devices having circular shape structures (e.g. round electrode pads), the characteristic dimension refers to the diameter of the round electrodes. For the devices having thin, rectangular lines as basic structures, the characteristic dimensions may refer to the width or length of these lines. As used herein, "microfluidic application" also encompass a process wherein the moiety is manipulated directly by a desirable force. It is not necessary that the force acts on the fluid to move the fluid and the movement of the fluid effects the manipulation of the moiety. For example, a moiety having a magnetic property can be manipulated by a magnetic force directly while the fluid may not be moved by the magnetic force. In other examples, the force can act on the fluid first and the movement of the fluid will effect the manipulation of the moiety. For example, a micropump can be used to move fluid, which in turn moves or manipulates the moiety contained in the fluid.

As used herein, "built-in structures on said substrate of a chip" means that the structures are built into the substrate or the structures are located on the substrate or the structures are structurally linked to the substrate of the chip. In one embodiment, the built-in structures may be fabricated on the substrate. For example, as described in "Dielectrophoretic manipulation of cells using spiral electrodes by Wang et al., *Biophys. J.*, 72:1887-1899 (1997)", spiral electrodes are fabricated on a glass substrate. Here the spiral electrodes are "built-in" structures on the glass substrate. In another embodiment, the "built-in" structures may be first fabricated on one substrate and the structure-containing first substrate may then be attached or bound to a second substrate. Such structures are "built-in" structures not only on the first substrate but also on the second substrate. In still another embodiment, the built-in structures may be attached or bound to the substrate. For example, thin, electrically-conductive wires may be used as electrodes for producing electric field. These electric wires may be bound or attached to a glass substrate. In this case, the electrically-conductive wires are "built-in" structures on the glass substrate. Throughout this application, when it is described that "built-in" structures on the chip or on the substrate are capable of generating physical forces and/or physical fields or these structures generate physical forces and/or physical fields, these structures are used in combination with external signal sources or external energy sources.

As used herein, "structures internal to said apparatus" means that the structures are integral parts of and structurally linked to other parts of the apparatus, or the structures are not separated or separable from other structural elements of the apparatus. For example, such internal structures can be microfabricated or otherwise attached to the substrate or other structural element(s) of the apparatus. Any "built-in structures on said substrates" described above are "structures internal to said apparatus" as long as the said apparatus comprise the substrates. Any built-in structures on a chip are "structures internal to said apparatus" as long as the said apparatus comprise the chip. Throughout this application, when it is described that "internal" structures of apparatus are capable of generating physical forces and/or physical fields or these structures generate physical forces and/or physical fields, these structures are used in combination with external signal sources or external energy sources.

As used herein, "micro-scale structures" means that the scale of the internal structures of the apparatus for exerting desired physical forces must be compatible with and useable in microfluidic applications and have characteristic dimensions of basic structural elements in the range from about 1 micron to about 20 mm scale.

As used herein, "moiety" refers to any substance whose analysis, isolation, manipulation, measurement, quantification or detection using the present microdevice is desirable. Normally, the dimension (or the characteristic dimensions) of the moiety should not exceed 1 cm. For example, if the moiety is spherical or approximately spherical, the dimension of the moiety refers to the diameter of the sphere or an approximated sphere for the moiety. If the moiety is cubical or approximately cubical, then the dimension of the moiety refers to the side width of the cube or an approximated cube for the moiety. If the moiety has an irregular shape, the dimension of the moiety may refer to the average between its largest axis and smallest axis. Non-limiting examples of moieties include cells, cellular organelles, viruses, particles, molecules, e.g., proteins, DNAs and RNAs, or an aggregate or complex thereof.

Moieties to be analyzed, isolated, manipulated, measured, quantified or detected include many types of particles—solid (e.g., glass beads, latex particles, magnetic beads), liquid (e.g., liquid droplets) or gaseous particles (e.g., gas bubble), dissolved particles (e.g., molecules, proteins, antibodies, antigens, lipids, DNAs, RNAs, molecule-complexes), suspended particles (e.g., glass beads, latex particles, polystyrene beads). Particles can be organic (e.g., mammalian cells or other cells, bacteria, virus, or other microorganisms) or inorganic (e.g., metal particles). Particles can be of different shapes (e.g., sphere, elliptical sphere, cubic, discoid, needle-type) and can be of different sizes (e.g., from nano-meter-size gold sphere, to micrometer-size cells, to millimeter-size particle-aggregate). Examples of particles include, but are not limited to, biomolecules such as DNA, RNA, chromosomes, protein molecules (e.g., antibodies), cells, colloid particles (e.g., polystyrene beads, magnetic beads), any biomolecules (e.g., enzyme, antigen, hormone etc). One specific type of particles refers to complexes formed between moieties and their binding partners, as described in a co-pending US Patent application entitled "METHODS FOR MANIPULATING MOIETIES IN MICROFLUIDIC SYSTEMS" (U.S. patent application Ser. No. 09/636,104, by Wang et al., filed on Aug. 10, 2000). The examples of such complexes include particle-particle complexes, particle-molecule complexes (e.g., cell-magnetic bead complexes formed by binding of the cells onto antibody-coated beads through the interaction between the antigens or protein molecules on cell surfaces and the antibody molecules immobilized on the magnetic bead surfaces; DNA molecule-magnetic bead complexes formed by immobilizing DNA molecules on magnetic bead surfaces, or protein molecule-polystyrene bead complexes formed by covering polystyrene bead surfaces with protein molecules). The methods disclosed in a co-pending U.S. patent application "METHODS FOR MANIPULATING MOIETIES IN MICROFLUIDIC SYSTEMS" (U.S. patent application Ser. No. 09/636,104, by Wang et al., filed on Aug. 10, 2000) may be used for manipulating moieties and/or binding partner-moiety complexes in the devices and apparatus in the present invention. The co-pending U.S. patent application "METHODS FOR MANIPULATING MOIETIES IN MICROFLUIDIC SYSTEMS" (U.S. patent application Ser. No. 09/636, 104) by Wang et al, filed on Aug. 10, 2000 is incorporated by reference in their entirety. These moieties can be isolated, manipulated, measured, quantified or detected using a microdevice of the present application.

As used herein, "plant" refers to any of various photosynthetic, eucaryotic multi-cellular organisms of the kingdom Plantae, characteristically producing embryos, containing chloroplasts, having cellulose cell walls and lacking locomotion.

As used herein, "animal" refers to a multi-cellular organism of the kingdom of Animalia, characterized by a capacity for locomotion, nonphotosynthetic metabolism, pronounced response to stimuli, restricted growth and fixed bodily structure. Non-limiting examples of animals include birds such as chickens, vertebrates such fish and mammals such as mice, rats, rabbits, cats, dogs, pigs, cows, ox, sheep, goats, horses, monkeys and other non-human primates.

As used herein, "bacteria" refers to small prokaryotic organisms (linear dimensions of around 1 micron) with non-compartmentalized circular DNA and ribosomes of about 70S. Bacteria protein synthesis differs from that of eukaryotes. Many anti-bacterial antibiotics interfere with bacteria proteins synthesis but do not affect the infected host.

As used herein, "eubacteria" refers to a major subdivision of the bacteria except the archaebacteria. Most Gram-positive bacteria, cyanobacteria, mycoplasmas, enterobacteria, pseudomonas and chloroplasts are eubacteria. The cytoplasmic membrane of eubacteria contains ester-linked lipids; there is peptidoglycan in the cell wall (if present); and no introns have been discovered in eubacteria.

As used herein, "archaebacteria" refers to a major subdivision of the bacteria except the eubacteria. There are three main orders of archaebacteria: extreme halophiles, methanogens and sulphur-dependent extreme thermophiles. Archaebacteria differs from eubacteria in ribosomal structure, the possession (in some case) of introns, and other features including membrane composition.

As used herein, "virus" refers to an obligate intracellular parasite of living but non-cellular nature, consisting of DNA or RNA and a protein coat. Viruses range in diameter from about 20 to about 300 nm. Class I viruses (Baltimore classification) have a double-stranded DNA as their genome; Class II viruses have a single-stranded DNA as their genome; Class III viruses have a double-stranded RNA as their genome; Class IV viruses have a positive single-stranded RNA as their genome, the genome itself acting as mRNA; Class V viruses have a negative single-stranded RNA as their genome used as a template for mRNA synthesis; and Class VI viruses have a positive single-stranded RNA genome but with a DNA intermediate not only in replication but also in MRNA synthesis. The majority of viruses are recognized by the diseases they cause in plants, animals and prokaryotes. Viruses of prokaryotes are known as bacteriophages.

As used herein, "fungus" refers to a division of eucaryotic organisms that grow in irregular masses, without roots, stems, or leaves, and are devoid of chlorophyll or other pigments capable of photosynthesis. Each organism (thallus) is unicellular to filamentous, and possesses branched somatic structures (hyphae) surrounded by cell walls containing glucan or chitin or both, and containing true nuclei.

As used herein, "binding partners" refers to any substances that bind to the moieties with desired affinity or specificity. Non-limiting examples of the binding partners include cells, cellular organelles, viruses, particles, microparticles or an aggregate or complex thereof, or an aggregate or complex of molecules, or specific molecules such as antibodies, single stranded DNAs. The binding partner can be a substance that is coated on the surface of a microdevice of the present invention. Alternatively, the binding partner can be a substance that is incorporated, e.g., microfabricated, into the material composition of the surface layer or bulk structure of the microdevice. The material composition of the surface layer or bulk structure of a microdevice may possess binding affinity to certain moiety, and thus functioning a binding partner itself.

As used herein, "an element that facilitates and/or enables manipulation of the microdevice and/or a moiety/microdevice complex" refers to any substance that is itself manipulatable or makes the moiety/microdevice complex manipulatable with the desired physical force(s). Non-limiting examples of the elements include cells, cellular organelles, viruses, particles, microparticles or an aggregate or complex thereof, or an aggregate or complex of molecules.

As used herein, "microparticles" refers to particles of any shape, any composition, any complex structures that are manipulatable by desired physical force(s) in microfluidic settings or applications. One example of microparticles is magnetic beads that are manipulatable by magnetic forces. Another example of microparticles is a cell that is manipulatable by an electric force such as a traveling-wave dielectrophoretic force. The microparticles used in the methods can have a dimension from about 0.01 micron to about ten centimeters. Preferably, the microparticles used in the methods have a dimension from about 0.01 micron to about several thousand microns. Examples of the microparticles include, but are not limited to, plastic particles, polystyrene microbeads, glass beads, magnetic beads, hollow glass spheres, particles of complex compositions, microfabricated free-standing microstructures, etc. The microdevice of the present invention is an example of a microparticle. Other particles include cells, cell organelles, large biomolecules such as DNA, RNA and proteins etc.

As used herein, "manipulation" refers to moving or processing of the moieties, and the microdevices disclosed in the present invention, which results in one-, two- or three-dimensional movement of the moiety and/or the microdevices. manipulation can be conducted in chip or non-chip format. When conducted in a chip format, it can be conducted within a single chip or between or among multiple chips, or on a substrate or among substrates of an apparatus. "Manipulation" of moieties and/or the microdevices can also be performed in liquid containers. Non-limiting examples of the manipulations include transportation, focusing, enrichment, concentration, aggregation, trapping, repulsion, levitation, separation, sorting, fractionation, isolation, or linear or other directed motion of the moieties. For effective manipulation, the characteristics of the moiety and/or the microdevices to be manipulated and the physical force used for manipulation must be compatible. For example, microdevices with certain magnetic properties can be used with magnetic force. In a specific example, the microdevice can comprise one or more types of magnetic materials, such ferro- or ferri-magnetic materials in the middle of the substrate. Exemplary ferro-or ferri-magnetic materials can be nickel metal or CoTaZr (Cobalt-Tantalum-Zirconium) alloy. Similarly, microdevices with electric charge(s) can be used with electrostatic (i.e. electrophoretic) force. In the case of manipulating microdevice-binding partner-moiety complexes, the characteristics of the moiety, or its binding partner or the microdevices, and the physical force used for manipulation must be compatible. For example, moiety or its binding partner or the microdevices with certain dielectric properties to induce dielectric polarization in the moiety or its binding partner or the microdevices can be used with dielectrophoresis force.

As used herein, "the moiety is not directly manipulatable" by a particular physical force means that no observable movement of the moiety can be detected when the moiety itself not coupled to a binding partner or a microdevice is acted upon by the particular physical force.

As used herein, "physical force" refers to any force that moves the moieties or their binding partners or the corresponding microdevices without chemically or biologically reacting with the moieties and the microdevice and/or binding partners, or with minimal chemical or biological reactions with the microdevices, binding partners and the moieties so that the biological/chemical functions/properties of the microdevices, binding partners and the moieties are not substantially altered as a result of such reactions. Throughout the application, the term "forces" or "physical forces" always means the "forces" or "physical forces" exerted on a moiety or moieties, the binding partner(s) and/or the microdevice(s). The "forces" or "physical forces" are always generated through "fields" or "physical fields". The forces exerted on moieties, the binding partner(s) and/or the microdevice(s) by the fields depend on the properties of the moieties, the binding partner(s) and/or the microdevice(s). Thus, for a given field or physical field to exert physical forces on a moiety, it is necessary for the moiety to have certain properties. While certain types of fields may be able to exert forces on different types of moieties having different properties, other types of fields may be able to exert forces on only limited type of moieties. For example, magnetic field can exert magnetic forces only on magnetic particles, e.g., microdevices or moieties having certain magnetic properties, but not on other microdevices or particles, e.g., polystyrene beads. The magnetic microdevices can be made by, e.g., incorporating magnetic materials such as ferro-or ferri-magnetic materials, into the microdevices. On the other hand, a non-uniform electric field can exert physical forces on many types of moieties such as polystyrene beads, cells, and also magnetic particles. It is not necessary for the physical field to be able to exert forces on different types of moieties or different moieties. But it is necessary for the physical field to be able to exert force on at least one type of moiety or at least one moiety, the binding partner(s) and/or the microdevice(s).

As used herein, "electric forces (or electrical forces)" are the forces exerted on moieties, the binding partner(s) and/or the microdevice(s) by an electric (or electrical) field.

As used herein, "magnetic forces" are the forces exerted on moieties, the binding partner(s) and/or the microdevice(s) by a magnetic field.

As used herein, "acoustic forces (or acoustic radiation forces)" are the forces exerted on moieties, the binding partner(s) and/or the microdevice(s) by an acoustic field.

As used herein, "optical (or optical radiation) forces" are the forces exerted on moieties, the binding partner(s) and/or the microdevice(s) by an optical field.

As used herein, "mechanical forces" are the forces exerted on moieties, the binding partner(s) and/or the microdevice(s) by a velocity field.

As used herein, "the moiety to be manipulated is substantially coupled onto the surface of the binding partner" means that a certain percentage, and preferably a majority, of the moiety to be manipulated is coupled onto the surface of the binding partner and can be manipulated by a suitable physical force via manipulation of the binding partner in the microdevice. Ordinarily, at least 0.5% of the moiety to be manipulated is coupled onto the surface of the binding partner. Preferably, at least 1%, 2%, 3%, 4%, 5%, 10%, 20%, 30%, 40%, 50%, 60%, 70%, 80% or 90% of the moiety to be manipulated is coupled onto the surface of the binding partner. The percentage of the coupled moiety includes the percentage of the moiety coupled onto the surface of a particular type of binding partner or a plurality of binding partners. When a plurality of binding partners is used, the moiety can be coupled onto the surface of the plurality of binding partners simultaneously or sequentially.

As used herein, "the moiety to be manipulated is completely coupled onto the surface of the binding partner" means that at least 90% of the moiety to be manipulated is coupled onto the surface of the binding partner in the microdevice. Preferably, at least 91%, 92%, 93%, 94%, 95%, 96%, 97%, 98%, 99% or 100% of the moiety to be manipulated is coupled onto the surface of the binding partner. The percentage of the coupled moiety includes the percentage of the moiety coupled onto the surface of a particular type of binding partner or a plurality of binding partners. When a plurality of binding partners is used, the moiety can be coupled onto the surface of the plurality of binding partners simultaneously or sequentially.

As used herein, "intracellular moiety" refers to any moiety that resides or is otherwise located within or attached to a cell, i.e., located in the cytoplasm or matrix of cellular organelles, attached to any intracellular membrane, resides or is otherwise located within periplasma, if there is one, or resides in or is otherwise located on the cell surface, i.e., attached on the outer surface of the cytoplasm membrane or cell wall, if there is one.

As used herein, "said photorecognizable coding pattern corresponds to an entity to be synthesized on said microdevice" means that the entity to be synthesized on a particular microdevice is predetermined according to the photorecognizable coding pattern on that microdevice. The coding pattern can determine the entity to be synthesized on a microdevice in different ways. For example, a coding pattern can have multiple digits and each digit determines a particular synthesis reaction and the collection of all digits collectively determines all synthesis reactions, and hence the identity of the entity to be synthesized. Alternatively, a coding pattern can be an "intact" pattern, i.e., the entire pattern, not a portion or a digit of the pattern, determines the entire synthesis reactions on the microdevice, and hence the identity of the entity to be synthesized.

As used herein, "said microdevices are sorted after each synthesis cycle according to said photorecognizable coding patterns" means that the synthetic steps or orders for making an entity on a particular microdevice are predetermined according to the photorecognizable coding pattern on that microdevice and after each synthesis cycle, the photorecognizable coding patterns on the microdevice is assessed for directing the next synthetic step or order.

As used herein, "sample" refers to anything which may contain a moiety to be analyzed, isolated, manipulated, measured, quantified or detected by the present microdevices and/or methods. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). The sample may also be a mixture of target analyte or enzyme containing molecules prepared in vitro. The sample may also be an environmental or agricultural sample derived from air, water such as river, lake, or ocean, soil, mountains or forests, etc.

As used herein, a "liquid (fluid) sample" refers to a sample that naturally exists as a liquid or fluid, e.g., a biological fluid. A "liquid sample" also refers to a sample that naturally exists in a non-liquid status, e.g., solid or gas, but is prepared as a liquid, fluid, solution or suspension containing the solid or gas sample material. For example, a liquid sample can encompass a liquid, fluid, solution or suspension containing a biological tissue, biological cells or other types of biological molecules.

As used herein the term "assessing (or assessed)" is intended to include quantitative and qualitative determination of the identity of a moiety, e.g., a protein or nucleic acid, present in the sample, and also of obtaining an index, ratio, percentage, visual or other value indicative of the identity of a moiety in the sample. Assessment may be direct or indirect.

B. Microdevices

In one aspect, the present invention is directed to a microdevice, which microdevice comprises: a) a substrate; and b) a photorecognizable coding pattern on said substrate. Preferably, the microdevice does not comprise an anodized metal surface layer, e.g., an anodized aluminium surface layer.

Any suitable substrate can be used in the microdevice. For example, the substrate can comprise silicon, e.g., silicon dioxide or silicon nitride, plastic, glass, ceramic, rubber, polymer, in its internal structure or on its surface, and a combination thereof The substrate can comprise multiple layers such as 3, 4 or more layers. For example, a substrate can have 3 layers. The top and the bottom layers can be made of same material, e.g., $SiO_2$ (or glass) and the middle layer can contain magnetic material(s). Alternatively, the top and the bottom layers can have different materials.

The substrate can comprises a surface that is hydrophobic or hydrophilic. The substrate can be in any suitable shape such as sphere, square, rectangle, triangle, circular disc, cube-like shape, cube, rectangular parallelepiped (cuboid), cone, cylinder, prism, pyramid, right circular cylinder and other regular or irregular shape. The substrate can be in any suitable dimension(s). For example, the thickness of the substrate can be from about 0.1 micron to about 500 microns. Preferably, the thickness of the substrate can be from about 1 micron to about 200 microns. More preferably, the thickness of the substrate can be from about 1 micron to about 50 microns. In a specific embodiment, the substrate is a rectangle having a surface area from about 10 squared-microns to about 1,000,000 squared-microns (e.g., 1000 micron by 1000 micron). In another specific embodiment, the substrate is a circular disc having a diameter from about 10 microns to about 500 microns. In still another specific embodiment, the substrate is in a cube-like shape having a side width from about 10 microns to about 100 microns. In yet another specific embodiment, the substrate is in an irregular shape having a single-dimension from about 1 micron to about 500 microns. In a preferred embodiment, the substrate is a composite comprising silicon, metal film and polymer film. In another preferred embodiment, the substrate can comprise a silicon layer and a metal layer, e.g., an aluminum layer. More preferably, the metal layer can comprise a magnetic material, such as nickel metal or CoTaZr (Cobalt-Tantalum-Zirconium) alloy.

The photorecognizable coding pattern can be based on any suitable photorecognizable (optical) property constructed on the substrate. For example, the photorecognizable coding pattern can be a photorecognizable (optical) property constructed on the material composition of the substrate itself, a hole in the substrate or a substance located, deposited or immobilized on the substrate, said substance having an optical refractive property that is different from the optical refractive property of the substrate. The substrate can be patterned. In addition, the surface layer of the substrate or microdevice can be modified. The versatility of the photorecognizable coding pattern can be caused by the shape, number, position distribution, optical refractive property, material composition, or a combination thereof, of the substrate, the hole(s), or the substance(s) located, deposited or immobilized on the substrate. In one exemplary microdevice, the substrate can have 4 layers. The top and the bottom layers can be made of same material, e.g., $SiO_2$ (or glass). One of the middle layers can contain magnetic material(s), e.g., magnetic alloys. The other middle lay can contain a photorecognizable coding pattern as a encoding layer. Preferably, the magnetic layer and the encoding layer does not substantially overlap, or not overlap at all, to ensure optical detection of the photorecognizable coding pattern in the encoding layer. Alternatively, the top and the bottom layer can have different materials. Exemplary patterns include numbers, letters, structures, 1-D and 2-D barcodes.

Although the microdevice can comprise a single photorecognizable coding pattern, it can also comprise a plurality of photorecognizable coding patterns, e.g. a plurality of the holes and/or a plurality of the substances.

To facilitate optical analysis (or photo-analysis) of encoding patterns, certain microdevices may incorporate "orientation" marks or alignment markers. For example, for the microdevices having thin circular disk shapes, the microdevices lying flat on either of its major surfaces will look identical, causing difficulties in identification. Therefore, the orientation markers can be used for indicating which major surface is being looked at when the microdevices are lying up and for helping decode the patterns.

The photorecognizable coding pattern can be constructed on the substrate according to any methods known in the art. For example, the photorecognizable coding pattern can be fabricated or microfabricated on the substrate. Any suitable fabrication or microfabrication method can be used including lithography such as photolithography, electron beam lithography and X-ray lithography (WO 96/39937 and U.S. Pat. Nos. 5,651,900, 5,893,974 and 5,660,680). For example, the fabrication or microfabrication methods can be used directly on the substrate to produce desirable patterns such as numbers, letters, structures, 1-D and 2-D barcodes.

If a substance having an optical refractive property that is different from the optical refractive property of the substrate is used as the photorecognizable coding pattern, the substance can be deposited or immobilized on the substrate by any suitable methods known in the art. For example, the substance can be deposited or immobilized on the substrate by evaporation or sputtering methods. The substance can be deposited or immobilized on the substrate directly or via a linker, e.g., a cleavable linker. The fabrication or microfabrication methods can be used on the substances deposited on the substrate to produce desirable patterns such as numbers, letters, structures, 1-D and 2-D barcodes. The substance can be immobilized deposited or on the substrate via a covalent or a non-covalent linkage. The substance can be deposited or immobilized on the substrate via specific or non-specific binding. Preferably, the linkage between the substance and the substrate can be a cleavable linkage such as a linkage cleavable by a chemical, physical or an enzymatic treatment.

In choosing the type, materials, compositions, structures and sizes of the microdevices, these properties or parameters of the microdevices should be compatible with the isolation, manipulation or detection format in the specific applications. For example, the microdevices may be used to isolate target analyte-molecules (e.g. proteins) from a molecule mixture. If the isolation uses dielectrophoretic forces, then the microdevices should have the desired dielectric properties. If the isolation/manipulation utilizes magnetic forces, then the microdevices should have incorporated magnetic materials such as ferro-or ferri-magnetic materials.

The microdevice can also comprise a binding partner that is capable of binding to a moiety to be isolated, manipulated or detected. Preferably, the binding partner specifically binds to the moiety. Throughout this application, whenever the binding partners are described or used, they are always coupled onto the microdevices of the present inventions. For example, when the complexes between the binding partners and the moieties to be manipulated are discussed, the complexes between the moieties and the binding partners that are coupled on the microdevices are referred to.

Any suitable binding partner including the binding partners disclosed in the co-pending U.S. patent application Ser. Nos. 09/636,104, filed Aug. 10, 2000 and Ser. No. 09/679,024, filed Oct. 4, 2000, the disclosures of which are incorporated by reference in its entirety, can be used. For example, the binding partners can be cells such as animal, plant, fungus or bacterium cells; cellular organelles such as nucleus, mitochondria, chloroplasts, ribosomes, ERs, Golgi apparatuses, lysosomes, proteasomes, secretory vesicles, vacuoles or microsomes; viruses, microparticles or an aggregate or complex thereof. Other binding partners may be molecules that have been immobilized on the microdevices' surfaces. For example, antibodies can be immobilized or bound on to the microdevices' surfaces. The antibody-bound microdevices can then be used to capture and bind to target proteins in a molecule mixture or to capture and bind to target cells in a cell mixture. Oligo-dT (e.g. 25 mer of T) can be immobilized onto the microdevices' surfaces. The oligo-dT bound microdevices can then be used to capture mRNA from a molecule mixture. Other molecules may be used as binding partners for capturing or binding DNA molecules. Nucleic acid fragments, e.g., DNA, RNA, PNA segments of specific sequences, may be used to hybridize to target nucleic acid, DNA, RNA or PNA, molecule.

Preferably, the microparticles used in the present microdevices have a dimension from about 0.01 micron to about several thousand microns. Non-limiting examples of the microparticles used in the microdevices include plastic particles, polystyrene microbeads, glass beads, magnetic beads, hollow glass spheres, metal particles, particles of complex compositions, microfabricated free-standing microstructures (e.g., Design of asynchronous dielectric micrometers by Hagedorn et al., in Journal of Electrostatics, 1994, Volume: 33, Pages 159-185). Particles of complex composition refer to particles that comprise or consist of multiple compositional elements, for example, a metallic sphere covered with a thin layer of non-conducting polymer film. In anther example, the particles may comprise a plastic sphere covered with a conductive polymer layer, which is in turn covered by an insulating polymer layer.

In choosing binding partners, the type, material, composition, structure and size of the binding partners may need to be compatible with the isolation, manipulation or detection format in the specific applications. This is especially important when the properties of the microdevices can not be controlled to fit specific applications. For example, magnetic beads may be used as binding partners if the means for manipulating moiety-binding-partner-microdevices are magnetic field-based. Beads having appropriate dielectric properties may be used if dielectrophoretic field is used for manipulating moiety-binding-partner-microdevices. However, if the microdevices comprise an element that facilities manipulation by a desirable force, the binding partner does not need to contain such an element. For example, if a microdevice contains a magnetic material, it is not necessary for a binding partner to have any magnetic materials for manipulation via a magnetic force. Similarly, if a microdevice contains a conductive material, it is not necessary for a binding partner to have any conductive materials for manipulation via a dielectrophoretic force.

The choice of the beads is further related with specific isolation, manipulation or detection details. For example, for separating target moiety from a mixture of molecules and particles by dielectrophoresis manipulation, binding partner's or microdevice's dielectric properties should be significantly different from those of molecules and particles so that when binding partners are coupled with the target moiety, the moiety-binding-partner-microdevices complexes may be selectively manipulated by dielectrophoresis. In an example of separating target cancer cells from a mixture of normal cells, the cancer cells may have similar dielectric properties to those of normal cells and all the cells behave similarly in their dielectrophoretic responses, e.g., negative dielectrophoresis. In this case, the binding partners or the microdevice preferably should be more dielectrically-polarizable than their suspending medium and will exhibit positive dielectrophoresis. Thus, such microdevices-binding partners-cancer-cell complexes can be selectively manipulated through positive dielectrophoresis forces while other cells experience negative dielectrophoresis forces.

The microdevice can comprise a single binding partner. Alternatively, it can be used in a high throughput analysis and can comprise a plurality of binding partners capable of binding or specifically binding to different moieties to be isolated, manipulated or detected.

The microdevice can further comprise an element that facilitates and/or enables manipulation of the microdevice and/or a moiety/microdevice complex. Any suitable element can be used. For example, the element can be magnetic materials to facilitate and/or enable manipulation by magnetic force, conductive or insulating materials to facilitate and/or enable manipulation by dielectrophoresis force, materials having high or low acoustic impedance to facilitate and/or enable manipulation by acoustic force, or charged materials to facilitate and/or enable manipulation by electrostatic force, etc. The element can be a cell, a cellular organelle, a virus, a microparticle, an aggregate or complex of molecules and an aggregate or complex thereof. In addition, the binding partners disclosed above and disclosed in the co-pending U.S. patent application Ser. No. 09/636,104, filed Aug. 10, 2000 can also be used as the element(s) that facilitates and/or enables manipulation of the microdevice and/or a moiety/microdevice complex.

The element can facilitate and/or enable manipulation of the microdevice and/or a moiety/microdevice complex by any suitable physical force including the physical forces disclosed in the co-pending U.S. patent application Ser. No. 09/636,104, filed Aug. 10, 2000. For instances, a dielectrophoresis force, a traveling-wave dielectrophoresis force, a magnetic force such as one effected via a magnetic field generated by a ferromagnetic material or one effected via a microelectromagnetic unit, an acoustic force such as one effected via a standing-wave acoustic field or a traveling-wave acoustic field, an electrostatic force such as one effected via a DC electric field, a mechanical force such as fluidic flow force, or an optical radiation force such as one effected via an optical intensity field generated by laser tweezers, can be used.

Dielectrophoresis refers to the movement of polarized particles, e.g., microdevices, microdevice-moiety complex, or microdevice-binding partner-moiety complex, in a non-uniform AC electrical field. When a particle is placed in an electrical field, if the dielectric properties of the particle and its surrounding medium are different, dielectric polarization will occur to the particle. Thus, the electrical charges are induced at the particle/medium interface. If the applied field is non-uniform, then the interaction between the non-uniform field and the induced polarization charges will produce a net force acting on the particle to cause particle motion towards the region of strong or weak field intensity. The net force acting on the particle is called dielectrophoretic force and the particle motion is dielectrophoresis. Dielectrophoretic force depends on the dielectric properties of the particles, particle surrounding medium, the frequency of the applied electrical field and the field distribution.

Traveling-wave dielectrophoresis is similar to dielectrophoresis in which the traveling-electric field interacts with the field-induced polarization and generates electrical forces acting on the particles. Particles, e.g., microdevices, microdevice-moiety complex, or microdevice-binding partner-moiety complex, are caused to move either with or against the direction of the traveling field. Traveling-wave dielectrophoretic forces depend on the dielectric properties of the particles and their suspending medium, the frequency and the magnitude of the traveling-field. The theory for dielectrophoresis and traveling-wave dielectrophoresis and the use of dielectrophoresis for manipulation and processing of microparticles may be found in various literatures (e.g., "Non-uniform Spatial Distributions of Both the Magnitude and Phase of AC Electric Fields determine Dielectrophoretic Forces by Wang et al., in *Biochim Biophys Acta* Vol. 1243, 1995, pages 185-194", "Dielectrophoretic Manipulation of Particles by Wang et al, in IEEE Transaction on Industry Applications, Vol. 33, No. 3, May/June, 1997, pages 660-669", "Electrokinetic behavior of colloidal particles in traveling electric fields: studies using yeast cells by Huang et al, in J. Phys. D: Appl. Phys., Vol. 26, pages 1528-1535", "Positioning and manipulation of cells and microparticles using miniaturized electric field traps and traveling waves. By Fuhr et al., in Sensors and Materials. Vol. 7: pages 131-146", "Dielectrophoretic manipulation of cells using spiral electrodes by Wang, X-B. et al., in *Biophys. J.* Volume 72, pages 1887-1899, 1997", "Separation of human breast cancer cells from blood by differential dielectric affinity by Becker et al, in Proc. Natl. Acad. Sci., Vol., 92, January 1995, pages 860-864"). The manipulation of microparticles with dielectrophoresis and traveling wave dielectrophoresis includes concentration/aggregation, trapping, repulsion, linear or other directed motion, levitation, and separation of particles. Particles may be focused, enriched and trapped in specific regions of the electrode reaction chamber. Particles may be separated into different subpopulations over a microscopic scale. Particles may be transported over certain distances. The electrical field distribution necessary for specific particle manipulation depends on the dimension and geometry of microelectrode structures and may be designed using dielectrophoresis theory and electrical field simulation methods.

The dielectrophoretic force $F_{DEPz}$ acting on a particle of radius r subjected to a non-uniform electrical field may be given, under dipole approximation, by $$F_{DEPz} = 2\pi \varepsilon_m r^3 \chi_{DEP} \nabla E_{rms}^2 \cdot \vec{a}_z$$

where $E_{rms}$ is the RMS value of the field strength, $\varepsilon_m$ is the dielectric permitivity of the medium. $\chi_{DEP}$ is the particle dielectric polarization factor or dielectrophoresis polarization factor, given, under dipole approximation, by $$\chi_{DEP} = \text{Re}\left(\frac{\varepsilon_p^* - \varepsilon_m^*}{\varepsilon_p^* + 2\varepsilon_m^*}\right).$$

"Re" refers to the real part of the "complex number". The symbol $$\varepsilon_x^* = \varepsilon_x - j\frac{\sigma_x}{2\pi f}$$

is the complex permitivity (of the particle x=p, and the medium x=m). The parameters $\varepsilon_p$ and $\sigma_p$ are the effective permitivity and conductivity of the particle, respectively. These parameters may be frequency dependent. For example, a typical biological cell will have frequency dependent, effective conductivity and permitivity, at least, because of cytoplasm membrane polarization.

The above equation for the dielectrophoretic force can also be written as $$F_{DEPz} = 2\pi \varepsilon_m r^3 \chi_{DEP} V^2 p(z) \vec{a}_z$$

where p(z) is the square-field distribution for a unit-voltage excitation (V=1 V) on the electrodes, V is the applied voltage.

There are generally two types of dielectrophoresis, positive dielectrophoresis and negative dielectrophoresis. In positive dielectrophoresis, particles are moved by dielectrophoresis forces towards the strong field regions. In negative dielectrophoresis, particles are moved by dielectrophoresis forces towards weak field regions. Whether particles exhibit positive and negative dielectrophoresis depends on whether the particles are more or less polarizable than the surrounding medium.

Traveling-wave DEP force refers to the force that is generated on particles or molecules due to a traveling-wave electric field. A traveling-wave electric field is characterized by the non-uniform distribution of the phase values of AC electric field components.

Here we analyze the traveling-wave DEP force for an ideal traveling-wave field. The dielectrophoretic force $F_{DEP}$ acting on a particle of radius r subjected to a traveling-wave electrical field $E_{TWD} = E\cos(2\pi(ft - z/\lambda_0))\vec{a}_x$ (i.e., a x-direction field is traveling along the z-direction) is given, under dipole approximation, by $$F_{TWD} = -2\pi \varepsilon_m r^3 \zeta_{TWD} E^2 \cdot \vec{a}_z$$

where E is the magnitude of the field strength, $\varepsilon_m$ is the dielectric permitivity of the medium. $\zeta_{TWD}$ is the particle polarization factor, given, under dipole approximation, by $$\zeta_{TWD} = \text{Im}\left(\frac{\varepsilon_p^* - \varepsilon_m^*}{\varepsilon_p^* + 2\varepsilon_m^*}\right).$$

"Im" refers to the imaginary part of the "complex number". The symbol $$\varepsilon_x^* = \varepsilon_x - j\frac{\sigma_x}{2\pi f}$$

is the complex permitivity (of the particle x=p, and the medium x=n). The parameters $\varepsilon_p$ and $\sigma_p$ are the effective permitivity and conductivity of the particle, respectively. These parameters may be frequency dependent.

Particles such as biological cells having different dielectric property (as defined by permitivity and conductivity) will experience different dielectrophoretic forces. For traveling-wave DEP manipulation of particles (including biological cells), traveling-wave DEP forces acting on a particle of 10 micron in diameter can vary somewhere between 0.01 and 10000 pN.

A traveling wave electric field can be established by applying appropriate AC signals to the microelectrodes appropriately arranged on a chip. For generating a traveling-wave-electric field, it is necessary to apply at least three types of electrical signals each having a different phase value. One method to produce a traveling wave electric field is to use four phase-quardrature signals (0, 90, 180 and 270 degrees) to energize four linear, parallel electrodes patterned on the chip surface. This set of four electrodes forms a basic, repeating unit. Depending on the applications, there may be more than two such units that are located next to each other. This will produce a traveling-electric field in the space above or near the electrodes. As long as electrode elements are arranged following certain spatially sequential orders, applying phase-sequenced signals will result in establishment of traveling electrical fields in the region close to the electrodes.

Both dielectrophoresis and traveling-wave dielectrophoresis forces acting on particles, e.g., microdevices, microdevice-moiety complex, or microdevice-binding partner-moiety complex, depend on not only the field distributions (e.g., the magnitude, frequency and phase distribution of electrical field components; the modulation of the field for magnitude and/or frequency) but also the dielectric properties of the particles and the medium in which particles are suspended or placed. For dielectrophoresis, if particles are more polarizable than the medium (e.g., having larger conductivities and/or permitivities depending on the applied frequency), particles will experience positive dielectrophoresis forces and be directed towards the strong field regions. The particles that are less polarizable than the surrounding medium will experience negative dielectrophoresis forces and be directed towards the weak field regions. For traveling wave dielectrophoresis, particles may experience dielectrophoresis forces that drive them in the same direction as the field is traveling direction or against it, dependent on the polarization factor $\zeta_{TWD}$. The following papers provide basic theories and practices for dielectrophoresis and traveling-wave-dielectrophoresis: Huang, et al., *J. Phys. D: Appl. Phys.* 26:1528-1535 (1993); Wang, et al., *Biochim. Biophys. Acta.* 1243:185-194 (1995); Wang, et al., *IEEE Trans. Ind. Appl.* 33:660-669 (1997).

Microparticles, e.g., microdevices, microdevice-moiety complex, or microdevice-binding partner-moiety complex, may be manipulated with magnetic forces. Magnetic forces refer to the forces acting on a particle due to the application of a magnetic field. In general, particles have to be magnetic or paramagnetic when sufficient magnetic forces are needed to manipulate particles. We consider a typical magnetic particle made of super-paramagnetic material. When the particle is subjected to a magnetic field $\overline{B}$, a magnetic dipole $\overline{\mu}$ is induced in the particle $$\overline{\mu} = V_p(\chi_p - \chi_m)\frac{B}{\mu_m},$$
$$= V_p(\chi_p - \chi_m)\overline{H}_m$$

where $V_p$ is the particle volume, $\chi_p$ and $\chi_m$ are the volume susceptibility of the particle and its surrounding medium, $\mu_m$ is the magnetic permeability of medium, $\overline{H}_m$ is the magnetic field strength. The magnetic force $F_{magnetic}$ acting on the particle is determined by the magnetic dipole moment and the magnetic field gradient:

$$\overline{F}_{magnetic} = 0.5 V_p(\chi_p - \chi_m)\overline{H}_m \bullet \nabla \overline{B}_m,$$

where the symbols "●" and "∇" refer to dot-product and gradient operations, respectively. Clearly, whether there is magnetic force acting on a particle depends on the difference in the volume susceptibility between the particle and its surrounding medium. Typically, particles are suspended in a liquid, non-magnetic medium (the volume susceptibility is close to zero) thus it is necessary to utilize magnetic particles (its volume susceptibility is much larger than zero). The particle velocity $\upsilon_{particle}$ under the balance between magnetic force and viscous drag is given by:

$$v_{particle} = \frac{\overline{F}_{magnetic}}{6\pi r \eta_m}$$

where r is the particle radius and $\eta_m$ is the viscosity of the surrounding medium. Thus to achieve sufficiently large magnetic manipulation force, the following factors should be considered: (1) the volume susceptibility of the magnetic particles should be maximized; (2) magnetic field strength should be maximized; and (3) magnetic field strength gradient should be maximized.

Paramagnetic particles are preferred whose magnetic dipoles are induced by externally applied magnetic fields and return to zero when external field is turned off. For such applications, commercially available paramagnetic or other magnetic particles may be used. Many of these particles range from submicron (e.g., 50 mn-0.5 micron) up to tens of microns. They may have different structures and compositions. One type of magnetic particle has ferromagnetic materials encapsulated in thin polymer layer, e.g., polystyrene. Another type of magnetic particle has ferromagnetic nano-particles filled into the poles of porous beads e.g., polystyrene beads. The surface of both types of these particles can be polystyrene in nature and may be modified to link to various types of molecules. In still another type of magnetic particle, ferro-magnetic materials can be incorporated uniformly into the particles during the polymerization process.

The manipulation of magnetic particles, microdevices, microdevice-moiety complex, or microdevice-binding partner-moiety complex, requires the generation of magnetic field distribution over microscopic scales. One desirable feature of a particle to be manipulated by magnetic force is that the particle has large magnetic susceptibility. Another desirable feature is that the particle has small residue magnetic polarization after the applied magnetic field/force is turned off. One approach for generating such magnetic fields is the use of microelectromagnetic units. Such units can induce or produce magnetic fields when an electrical current is applied. The on/off status and the magnitude of the electrical current applied to each unit will determine the magnetic field distribution. The structure and dimension of the microelectromagnetic units may be designed according to the requirement of the magnetic field distribution. Manipulation of magnetic particles includes the directed movement, focusing and trapping of magnetic particles. The motion of magnetic particles in a magnetic field is termed "magnetophoresis". Theories and practice of magnetophoresis for cell separation and other applications may be found in various literatures (e.g., Magnetic Microspheres in Cell Separation, by Kronick, P. L. in Methods of Cell Separation, Volume 3, edited by N. Catsimpoolas, 1980, pages 115-139; Use of magnetic techniques for the isolation of cells, by Safarik I. And Safarikova M., in J. of Chromatography, 1999, Volume 722(B), pages 33-53; A fully integrated micromachined magnetic particle separator, by Ahn C. H. et al., in J. of Microelectromechanical systems, 1996, Volume 5, pages 151-157).

Microparticles, e.g., microdevices, microdevice-moiety complex, or microdevice-binding partner-moiety complex, may be manipulated using acoustic forces, i.e., using acoustic fields. In one case, a standing-wave acoustic field is generated by the superimposition of an acoustic wave generated from an acoustic wave source and its reflective wave. Particles in standing-wave acoustic fields experience the so-called acoustic radiation force that depends on the acoustic impedance of the particles and their surrounding medium. Acoustic impedance is the product of the density of the material and the velocity of acoustic-wave in the material. Particles with higher acoustic impedance than the surrounding medium are directed towards the pressure nodes of the standing wave acoustic field. Particles experience different acoustic forces in different acoustic field distributions.

One method to generate an acoustic wave source is to use piezoelectric material. These materials, upon applying electrical fields at appropriate frequencies, can generate mechanical vibrations that are transmitted into the medium surrounding the materials. One type of piezoelectric material is piezoelectric ceramics. Microelectrodes may be deposited on such ceramics to activate the piezoelectric ceramic and thus to produce appropriate acoustic wave fields. Various geometry and dimensions of microelectrodes may be used according to the requirements of different applications. Reflective walls are needed to generate a standing-wave acoustic field. Acoustic wave fields of various frequencies may be applied, i.e., fields at frequencies between kHz and hundred megahertz. In another case, one could use a non-standing wave acoustic field, e.g., a traveling-wave acoustic field. A traveling-wave acoustic field may exert forces on particles (see e.g., see, "Acoustic radiation pressure on a compressible sphere, by K. Yoshioka and Y. Kawashima in Acustica, 1955, Vol. 5, pages 167-173"). Particles not only experience forces from acoustic fields directly but also experience forces due to surrounding fluid because the fluid may be induced to move by the traveling-wave acoustic field. Using acoustic fields, particles may be focussed, concentrated, trapped, levitated and transported in a microfluidic environment. Another mechanism for producing forces on particles in an acoustic field is through acoustic-induced fluid convection. An acoustic field produced in a liquid may induce liquid convection. Such convection is dependent on the acoustic field distribution, properties of the liquid, and the volume and structure of the chamber in which the liquid is placed. Such liquid convection will impose forces on particles placed in the liquid and those forces may be used for manipulating particles. One example where such manipulating forces may be exploited is for enhancing the mixing of liquids or the mixing of particles in a liquid. For the present invention, such convection may be used to enhance the mixing of the binding partners coupled onto the microdevices with moiety in a suspension and to promote the interaction between the moiety and the binding partners.

A standing plane wave of ultrasound can be established by applying AC signals to the piezoelectric transducers. For example, the standing wave spatially varying along the z axis in a fluid can be expressed as:

$$\Delta p(z) = p_0 \sin(kz)\cos(\omega t)$$

where $\Delta p$ is acoustic pressure at z, $p_0$ is the acoustic pressure amplitude, k is the wave number ($2\pi/\lambda$, where $\lambda$ is the wavelength), z is the distance from the pressure node, $\omega$ is the angular frequency, and t is the time. According to the theory developed by Yoshioka and Kawashima (see, "Acoustic radiation pressure on a compressible sphere, by K. Yoshioka and Y. Kawashima in Acustica, 1955, Vol. 5, pages 167-173"), the radiation force $F_{acoustic}$ acting on a spherical particle in the stationary standing wave field is given by (see "Studies on particle separation by acoustic radiation force and electrostatic force by Yasuda K. et al. in Jpn. J. Appl. Physics, 1996, Volume 35, pages 3295-3299")

$$F_{acoustic} = -\frac{4\pi}{3} r^3 k\, E_{acoustic}\, A\, \sin(2kz)$$

where r is the particle radius, $E_{acoustic}$ is the average acoustic energy density, A is a constant given by $$A = \frac{5\rho_p - 2\rho_m}{2\rho_p + \rho_m} - \frac{\gamma_p}{\gamma_m}$$

where $\rho_m$ and $\rho_p$ are the density of the particle and the medium, $\gamma_m$ and $\gamma_p$ are the compressibility of the particle and medium, respectively. A is termed herein as the acoustic-polarization-factor.

When A>0, the particle moves towards the pressure node (z=0) of the standing wave.

When A<0, the particle moves away from the pressure node.

Clearly, particles of different density and compressibility will experience different acoustic-radiation-forces when placed into the same standing acoustic wave field. For example, the acoustic radiation force acting on a particle of 10 micron diameter can vary somewhere between 0.01 and 1000 pN, depending on the established acoustic energy density distribution.

Piezoelectric transducers are made from "piezoelectric materials" that produce an electric field when exposed to a change in dimension caused by an imposed mechanical force (piezoelectric or generator effect). Conversely, an applied electric field will produce a mechanical stress (electrostrictive or motor effect) in the materials. They transform energy from mechanical to electrical and vice-versa. The piezoelectric effect was discovered by Pierre Curie and his brother Jacques in 1880. It is explained by the displacement of ions, causing the electric polarization of the materials' structural units. When an electric field is applied, the ions are displaced by electrostatic forces, resulting in the mechanical deformation of the whole material.

Microparticles, e.g., microdevices, microdevice-moiety complex, or microdevice-binding partner-moiety complex, may be manipulated using DC electric fields. A DC electric field can exert an electrostatic force on charged particles. The force depends on the charge magnitude and polarity of the particles as well as on the magnitude and direction of the field. The particles with positive and negative charges may be directed to electrodes with negative and positive potentials, respectively. By designing a microelectrode array in a microfluidic device, electric field distributions may be appropriately structured and realized. With DC electric fields, microparticles may be concentrated (enriched), focussed and moved (transported) in a microfluidic device. Proper dielectric coating may be applied on to DC electrodes to prevent and reduce undesired surface electrochemistry and to protect electrode surfaces.

The electrostatic force $F_E$ on a particle in an applied electrical field $E_z \vec{a}_z$ can be given by $$F_E = Q_p E_z \vec{a}_z$$

where $Q_p$ is the effective electric charge on the particle. The direction of the electrostatic force on a charged particle depends on the polarity of the particle charge as well as the direction of the applied field.

Thermal convection forces refer to the forces acting on particles, e.g., microdevices, microdevice-moiety complex, or microdevice-binding partner-moiety complex, due to the fluid-convection (liquid-convection) that is induced by a thermal gradient in the fluid. Thermal diffusion in the fluid drives the fluid towards thermal equilibrium. This causes a fluid convection. In addition, the density of aqueous solutions tends to decrease with increasing temperature. Such density differences are also not stable within a fluid resulting in convection. Thermal convection may be used to facilitate liquid mixing. Directed thermal convection may act as an active force.

Thermal gradient distributions may be established within a chip-based chamber where heating and/or cooling elements may be incorporated into the chip structure. A heating element may be a simple joule-heating resistor coil. Such a coil could be microfabricated onto the chip. As an example, consider a coil having a resistance of 10 ohm. Applying 0.2 A through the coil would result in 0.4 W joule heating-power. When the coil is located in an area <100 micron$^2$, this is an effective way of heat generation. Similarly, a cooling element may be a Peltier element that could draw heat upon applying electric potentials.

As an exemplary embodiment, the microdevices of the present invention may be used on a chip which incorporates an array of individually addressable heating elements. These heating elements may be positioned or structurally arranged in certain order so that when each, some or all of the elements are activated, thermal gradient distributions will be established to produce thermal convection. For example, if one heating element is activated, temperature increases in the liquid in the neighborhood of that element will induce fluid convection. In another exemplary embodiment, the chip may comprise multiple, interconnected heating units so that these units can be turned on or off in a synchronized order. Yet, in another example, the chip may comprise only one heating element that can be energized to produce heat and induce thermal convection in the liquid fluid.

Other physical forces may be applied. For example, mechanical forces, e.g., fluidic flow forces, may be used to transport microparticles, e.g., microdevices, microdevice-moiety complex, or microdevice-binding partner-moiety complex. Optical radiation forces as exploited in "laser tweezers" may be used to focus, trap, levitate and manipulate microparticles. The optical radiation forces are the so-called gradient-forces when a material (e.g., a microparticle) with a refractive index different from that of the surrounding medium is placed in a light gradient. As light passes through a polarizable material, it induces fluctuating dipoles. These dipoles interact with the electromagnetic field gradient, resulting in a force directed towards the brighter region of the light if the material has a refractive index larger than that of the surrounding medium. Conversely, an object with a refractive index lower than the surrounding medium experiences a force drawing it towards the darker region. The theory and practice of "laser tweezers" for various biological application are described in various literatures (e.g., "Making light work with optical tweezers, by Block S. M., in Nature, 1992, Volume 360, pages 493-496"; "Forces of a single-beam gradient laser trap on a dielectric sphere in the ray optics regime, by Ashkin, A., in Biophys. J., 1992, Volume 61, pages 569-582"; "Laser trapping in cell biology, by Wright et al., in IEEE J. of Quantum Electronics, 1990, Volume 26, pages 2148-2157"; "Laser manipulation of atoms and particles, by Chu S. in Science, 1991, Volume 253, pages 861-866"). The light field distribution and/or light intensity distribution may be produced with built-in optical elements and arrays on a chip and external optical signal sources, or may be produced with built-in electro-optical elements and arrays on a chip and the external structures are electrical signal sources. In the former case, when the light produced by the optical signal sources passes through the built-in optical elements and arrays, light is processed by these elements/arrays through, e.g., reflection, focusing, interference, etc. Optical field distributions are generated in the regions around the chip. In the latter case, when the electrical signals from the external electrical signal sources are applied to the built-in electro-optical elements and arrays, light is produced from these elements and arrays and optical fields are generated in the regions around the chip.

Although the microdevices can comprise a single element, they may also be used in high throughput analysis and preferably comprise a plurality of elements, each of the elements facilitates and/or enables manipulation of the microdevice and/or the moiety/microdevice complex by a different physical force. For example, the element can be a magnetic material for manipulation by a magnetic force, a conductive or insulating material for manipulation by a dielectrophoresis force, a material having high or low acoustic impedance for manipulation by acoustic force, and/or a charged material for manipulation by a electrostatic force, etc.

In a preferred embodiment, the microdevice comprises a binding partner that is capable of binding or specifically binding to a moiety to be isolated, manipulated or detected and an element that facilitates and/or enables manipulation of the microdevice and/or the moiety/microdevice complex. More preferably, the microdevice(s) comprises a plurality of binding partners, each of the binding partners is capable of binding or specifically binding to a different moiety to be isolated, manipulated or detected and a plurality of the elements, each of the elements facilitates and/or enables manipulation of the microdevice and/or the moiety/microdevice complex by a different physical force.

The microdevice can further comprise a detectable marker or a molecular tag. Exemplary detectable markers include dyes, radioactive substances and fluorescent substances. Exemplary detectable molecular tags include nucleic acid, oligonucleotide, protein and peptide sequences.

In a specific embodiment, the present invention is directed to a microdevice that does not comprise a porous surface. In another specific embodiment, the present invention is directed to a microdevice that comprises a metal or metal alloy layer and a non-metal surface layer. In still another specific embodiment, the present invention is directed to a microdevice that comprises a hole as the photorecognizable coding pattern and said hole does not penetrate through the entire depth of the substrate.

C. Methods, Kits and Arrays for Analyzing, Isolating, Manipulating and Detecting Moieties In one aspect, the present invention is directed to a method for isolating a moiety, which method comprises: a) providing a microdevice comprising a substrate, a photorecognizable coding pattern on said substrate and a binding partner that is capable of binding, and preferably specifically binding, to a moiety to be isolated; b) contacting a sample containing or suspected of containing said moiety with said microdevice provided in step a) under conditions allowing binding between said moiety and said binding partner; and c) recovering said microdevice from said sample, whereby the identity of said isolated moiety is assessed by photoanalysis of said photorecognizable coding pattern. Preferably, the microdevice used in the method does not comprise an anodized metal surface layer, e.g., an anodized aluminium surface layer.

Any moiety including the moieties disclosed in the above Section B can be isolated by the present method. For example, the moiety to be isolated can be a cell, a cellular organelle, a virus, a molecule and an aggregate or complex thereof.

Although the present method can be used to isolate a single moiety, it is preferably to be used in high throughput analysis and preferably a plurality of moieties are isolated by using a plurality of microdevices, each of the microdevices contains a binding partner that is capable of binding to a member of the plurality of the moieties.

A moiety in any suitable sample can be isolated. Preferably, the moiety to be isolated is contained in a fluid sample.

The isolation can be conducted in any suitable apparatus or device. For example, the isolation can be conducted in a liquid container such as a beaker, a flask, a cylinder, a test tube, a microcentrifuge tube, a centrifugation tube, a culture dish, a multiwell plate and a filter device. Alternatively, the isolation can be conducted in a chip format.

The method can further comprise a step of recovering said isolated moiety from said microdevice.

In another aspect, the present invention is directed to a method for manipulating a moiety, e.g., in a microfluidic application, which method comprises: a) providing a microdevice comprising a substrate, a photorecognizable coding pattern on said substrate and a binding partner that is capable of binding, and preferably specifically binding, to a moiety to be manipulated; b) coupling said moiety to said microdevice provided in step a) via binding between said moiety and said binding partner to form a moiety-microdevice complex; and c) manipulating said moiety-microdevice complex with a physical force in a chip format, thereby said moiety is manipulated. Preferably, the microdevice used in the method does not comprise an anodized metal surface layer, e.g., an anodized aluminium surface layer. Alternatively, the above manipulation method can be conducted in an off-chip format, e.g., in a liquid container.

Preferably, the manipulation is effected through a combination of a structure that is external to the chip and a structure that is built-in in the chip. For example, chips and structures internal and external to the chips that are disclosed in the co-pending U.S. patent application Ser. Nos. 09/636,104, filed Aug. 10, 2000 and Ser. No. 09/679, 024, filed Oct. 4, 2000, the disclosures of which are incorporated by reference in its entirety, can be used in the present method. For example, the methods can be used on silicon, silicon dioxide, silicon nitride, plastic, glass, ceramic, photoresist or rubber chips. In addition, the methods can be used on a chemchip, i.e., on which chemical reactions are carried out, a biochip, i.e., on which biological reactions are carried out, or a combination of a biochemchip.

The physical forces used in the present methods are effected through a combination of the structure that is external to the chip and the structure that is built-in in the chip. The external structures are energy sources that can be connected to the built-in structures for energizing the built-in structures to generate a physical force such as dielectrophoresis force, magnetic force, acoustic force, electrostatic force, mechanical force or optical radiation force. The built-in structures comprise a single unit or a plurality of units. Each unit is, when energized and in combination with the external structure, capable of effecting the physical force on the binding partner. In the case of a plurality of units, the built-in structure may further comprise the means for selectively energizing any one of the plurality of units.

In one example, when magnetic force is used to manipulate a complex of a moiety (e.g., DNA molecules) and a microdevice comprising its binding partner, the electromagnetic chip disclosed in the co-pending U.S. patent application Ser. No. 09/399, 299, filed Sep. 16, 1999, which is incorporated by reference in its entirety, can be used in the methods. Typically, such electromagnetic chips with individually addressable micro-electromagnetic units comprise: a substrate; a plurality of micro-electromagnetic units on the substrate, each unit capable of inducing a magnetic field upon application electric current; a means for selectively energizing any one of a plurality of units to induce a magnetic field therein. Preferably, the electromagnetic chips further comprise a functional layer coated on the surface of the chips for immobilizing certain types of molecules. In this example of magnetic manipulation of moiety-binding partner-microdevice complexes, microelectromagnetic units are the built-in structures internal to the chip and the electrical current source that is connected to the microelectromagnetic units is the structures external to the chip. When the electric current from the external current source is applied to the microelectromagnetic units, magnetic fields will be generated in the regions around the microelectromagnetic units and magnetic forces will be produced on magnetic particles that are present in the region around the microelectromagnetic units. Typically, for the case of the manipulation force being magnetic force, the built-in structures are electromagnetic units that are incorporated on the chip and the external structures are the electrical signal sources (e.g., current sources). When the appropriately designed and fabricated electromagnetic units are energized by the electrical signal sources, magnetic fields are generated in the regions around the chip. When the microdevice-binding partner-moiety complexes are subjected to such magnetic fields, magnetic forces are produced on them, and such forces are dependent on the magnetic field distribution, the magnetic properties of the microdevices or the binding partner or microdevice-binding partner-moiety complexes and the magnetic properties of the medium that surrounds the microdevices or microdevice-binding partner-moiety complexes.

In another example, when dielectrophoresis force and traveling-wave dielectrophoresis force are used to manipulate a complex of a moiety (e.g., protein molecules) and its binding partner coupled onto a microdevice (e.g., antibodies can be coupled onto microdevices' surfaces, allowing for binding of protein molecules), a spiral electrode array on a glass chip, together with a phase-quardrature AC electrical signal source, can be used in the method (see "Dielectrophoretic manipulation of cells using spiral electrodes by Wang, X-B. et al., in *Biophys. J.* Volume 72, pages 1887-1899, 1997"). In this example of dielectrophoretic manipulation of moiety-binding partner-microdevice complexes, a spiral electrode array is a built-in structure internal to the chip and the AC electrical signal source that is connected to the spiral electrodes is the structure external to the chip. When AC electrical signals of appropriate phases from the external signal source are applied to the spiral electrode array, electrical fields will be generated in the regions around the spiral electrode array. Dielectrophoretic and traveling-wave dielectrophoretic forces will be produced on moiety-binding partner-microdevice complexes that are present in the region around the spiral electrode array. Typically, for the case of the manipulation force being dielectrophoresis and/or dielectrophoresis force, the built-in structures are the electrode elements and electrode arrays that are incorporated on a chip and the external structures are electrical signal sources. When the appropriately designed electrode elements and electrode arrays are energized by the electrical signal sources, non-uniform electrical fields are generated in the regions around the chip. When the microdevice or microdevice-binding partner-moiety complexes are subjected to such non-uniform electrical fields, dielectrophoresis and/or traveling-wave dielectrophoresis forces acting on the microdevices or microdevice-binding partner-moiety complexes are produced. Such forces are dependent on the interaction between the electrical field distributions and field induced dielectric polarization in microdevices, microdevice-moiety complex, or microdevice-binding partner-moiety complex, etc.

In still another example, when acoustic force is used to manipulate a complex of a moiety (e.g., cells) and its binding partner coupled onto microdevices (e.g., antibodies immobilized on microdevices' surfaces, allowing for binding of cells), the phased array of piezoelectric transducers described in U.S. Pat. No. 6,029,518 by Oeftering, R. can be used in the methods. In this example of acoustic manipulation of moiety-binding partner-microdevice complexes, the phased array of piezoelectric transducers is a built-in structure internal to the chip and the AC electrical signal source that is connected to the phased array is the structure external to the chip. When AC electrical signals from the external signal source are applied to the phased array of piezoelectric transducers, acoustic wave will be generated from the piezoelectric transducers and transmitted into the regions around the piezoelectric transducer. Depending on the chamber structure comprising such a piezoelectric transducer, when moieties and moiety-binding partner-microdevice complexes in a liquid suspension are introduced into the chamber, acoustic radiation forces will be produced on moieties and moiety-binding partner-microdevice complexes. Typically, for the case of the manipulation force being acoustic forces, the built-in structures are the piezoelectric elements or structures that are incorporated on a chip and the external structures are electrical signal sources. When the appropriately designed piezoelectric elements or structures are energized by the electrical signal sources, acoustic waves are generated from piezoelectric elements or structures and acoustic-wave fields are produced in the regions around the chip. When the microdevices or microdevice-binding partner-moiety complexes are subjected to such acoustic fields, acoustic forces are produced on the microdevices or microdevice-binding partner-moiety complexes and such forces are dependent on acoustic-wave field distribution, acoustic properties of the microdevices or microdevice-binding partner-moiety complexes and acoustic properties of the medium that surrounds the microdevices or microdevice-binding partner-moiety complexes.

For the case of the manipulation force being electrostatic force, the built-in structures are the electrode elements and electrode arrays that are incorporated on a chip and the external structures are electrical signal sources (e.g., a DC current source). When the appropriately designed electrode elements and electrode arrays are energized by the electrical signal sources, electrical fields are generated in the regions around the chip. When the microdevice or microdevice-binding partner-moiety complexes are subjected to electrical fields, electrostatic forces acting on the microdevices or microdevice-binding partner-moiety complexes are produced. Such forces depend on the electrical field distributions and charge properties of the microdevices or microdevice-binding partner-moiety complexes.

For the case of the manipulation force being optical radiation force, in one example, the built-in structures are the optical elements and arrays that are incorporated on a chip and the external structures are optical signal sources (e.g., a laser source). When the light produced by the optical signal sources passes through the built-in optical elements and arrays, optical fields are generated in the regions around the chip and the optical field distribution is dependent on the geometrical structures, sizes and compositions of the built-in optical elements and arrays. When the microdevices or microdevice-binding partner-moiety complexes are subjected to optical fields, optical radiation forces acting on the binding partners or binding partner-moiety complexes are produced. Such forces depend on the optical field distributions and optical properties of the binding partners or binding partner-moiety complexes. In other examples, the built-in structures are the electro-optical elements and arrays that are incorporated on a chip and the external structures are electrical signal sources (e.g., a DC current source). When electrical signals from the external electrical signal sources are applied to the built-in electro-optical elements and arrays, light is produced from these elements and arrays and optical fields are generated in the regions around the chip. When the microdevices or microdevice-binding partner-moiety complexes are subjected to optical fields, optical radiation forces acting on the microdevices or microdevice-binding partner-moiety complexes are produced. Such forces depend on the optical field distributions and optical properties of the microdevices or microdevice-binding partner-moiety complexes.

For the case of the manipulation force being mechanical force, the built-in structures may be the electromechanical elements/devices that are incorporated on a chip and the external structures are electrical signal sources (e.g., a DC current source). The electromechanical devices may be a microfabricated pump that can generate pressure to pump fluids. When the appropriately designed electromechanical elements/devices are energized by the electrical signal sources, mechanical forces are exerted on the fluid that is introduced to the spaces around the chip (e.g., on the chip). Thus, the microdevices or microdevice-binding partner-moiety complexes in the fluid will experience mechanical forces. The forces on microdevices or microdevice-binding partner-moiety complexes depend on the mechanical forces on the fluid and depend on the size, composition and geometry of the microdevices or microdevice-binding partner-moiety complexes.

Any moiety including the moieties disclosed in the above Section B can be manipulated by the present method. For example, the moiety to be isolated can be a cell, a cellular organelle, a virus, a molecule and an aggregate or complex thereof.

The manipulation can be effected via any suitable physical force such as a dielectrophoresis, a traveling-wave dielectrophoresis, a magnetic, an acoustic, an electrostatic, a mechanical, an optical radiation and/or a thermal convection force.

The present method can be used for any type of suitable manipulation. Exemplary manipulations include transportation, focusing, enrichment, concentration, aggregation, trapping, repulsion, levitation, separation, fractionation, isolation and linear or other directed motion of the moiety.

In a preferred embodiment, the moiety is not directly manipulatable by a physical force. In another preferred embodiment, neither the moiety nor the binding partner is directly manipulatable by a physical force, and the microdevice contains an element that makes the microdevice or the moiety-microdevice complex manipulatable. Any such element including the elements disclosed in the above Section B can be used in the present method.

Although the present method can be used to manipulate a single moiety, it is preferably to be used in a high throughput analysis and preferably a plurality of moieties is manipulated. Preferably, the plurality of moieties is manipulated via a plurality of corresponding microdevices. The plurality of moieties can be manipulated sequentially or simultaneously.

The present method can also comprise a step of recovering said manipulated moiety from said microdevice and/or said chip. The present method can further comprise a step of assessing the identity of the manipulated moiety by photoanalysis of the photorecognizable coding pattern of the microdevice. The present method can still further comprise a step of assessing the identity of the recovered moiety by photoanalysis of the photorecognizable coding pattern of the microdevice.

In still another aspect, the present invention is directed to a kit for manipulating a moiety, e.g., in a microfluidic application, which kit comprises: a) a microdevice comprising a substrate, a photorecognizable coding pattern on said substrate and a binding partner that is capable of binding, and preferably specifically binding, to a moiety to be manipulated; and b) a chip on which a moiety-microdevice complex can be manipulated. Preferably, the kit can further comprise instruction(s) for coupling the moiety to the microdevice and/or for manipulating the moiety-microdevice complex on the chip. Also preferably, the microdevice used in the kit does not comprise an anodized metal surface layer, e.g., an anodized aluminium surface layer.

In yet another aspect, the present invention is directed to a method for detecting a moiety, which method comprises: a) providing a microdevice comprising a substrate, a photorecognizable coding pattern on said substrate and a binding partner that is capable of binding, and preferably specifically binding, to a moiety to be detected; b) contacting a sample containing or suspected of containing said moiety with said microdevice provided in step a) under conditions allowing binding between said moiety and said binding partner; and c) detecting binding between said moiety and said binding partner, whereby the presence or amount of said moiety is assessed by analysis of binding between said moiety and said binding partner and the identity of said moiety is assessed by photoanalysis of said photorecognizable coding pattern. Preferably, the microdevice used in the method does not comprise an anodized metal surface layer, e.g., an anodized aluminium surface layer.

The binding between the moiety and the binding partner can be detected by any suitable methods, devices or instruments. For example, the moiety can be labeled, e.g., with fluorescent, radioactive, enzymatic or other chemical labels. The moiety can be labeled before its binding with the binding partner or after its binding with the binding partner. In another example, the absorbance or other optical properties of the moiety can be used in detecting its binding with the binding partner. In still another example, the molecular weight of the moiety can be used in detecting its binding with the binding partner, e.g., by mass spectrometry such as MALDI-TOF. The detecting methods based on the labeling of the moiety can be conducted in a direct labeling method, i.e., the moiety to be detected is labeled, or in a competitive assay format, i.e., a labeled moiety or moiety analog is added to the sample containing a moiety to be detected. In yet another example, the moiety is cleaved off or recovered from, or isolated or purified from the moiety-binding partner complex before the detection. Any suitable methods, e.g., HPLC, can be used to isolate or purify the moiety.

Any moiety including the moieties disclosed in the above Section B can be detected by the present method. For example, the moiety to be detected can be a cell, a cellular organelle, a virus, a molecule and/or an aggregate or complex thereof.

Although the present method can be used to detect a single moiety, it is preferably to be used in a high throughput analysis and preferably a plurality of moieties is detected by using a plurality of microdevices, each of the microdevices contains a binding partner that is capable of binding to a member of the plurality of the moieties. The plurality of moieties can be detected sequentially or simultaneously.

The detection can be conducted in any suitable apparatus or device. For example, the detection can be conducted in a liquid container such as a beaker, a flask, a cylinder, a test tube, a microcentrifuge tube, a centrifugation tube, a culture dish, a multiwell plate and/or a filter device. Alternatively, the microdevice is placed or immobilized on a surface and the detection can be conducted in a chip format. Preferably, a plurality of microdevice is placed or immobilized on a surface and the detection can be conducted in a chip format.

A moiety in any suitable sample can be detected. Preferably, the moiety to be detected is contained in a fluid sample.

In yet another aspect, the present invention is directed to an array for detecting moieties, which array comprises a plurality of microdevices positioned, deposited or immobilized on a surface, e.g., a chip, each of said microdevices comprises a photorecognizable coding pattern on a substrate and a binding partner that is capable of binding, and preferably specifically binding, to a moiety to be detected. Preferably, at least one of the microdevices used in the array does not comprise an anodized metal surface layer, e.g., an anodized aluminium surface layer. More preferably, at least 50% or all of the microdevices used in the array do not comprise an anodized metal surface layer, e.g., an anodized aluminium surface layer. The microdevices can be positioned, deposited or immobilized on the surface or chip using any suitable methods such as being positioned on a surface by a magnetic force.

The present methods can be used for analyzing, isolating, manipulating or detecting any types of moieties when the moieties are involved in certain processes, such as physical, chemical, biological, biophysical or biochemical processes, etc., in a chip format or non-chip format. Moieties can be cells, cellular organelles, viruses, molecules or an aggregate or complex thereof. Moieties can be pure substances or can exist in a mixture of substances wherein the target moiety is only one of the substances in the mixture. For example, cancer cells in the blood from leukemia patients, cancer cells in the solid tissues from patients with solid tumors and fetal cells in maternal blood from pregnant women can be the moieties to be isolated, manipulated or detected. Similarly, various blood cells such as red and white blood cells in the blood can be the moieties to be isolated, manipulated or detected. DNA molecules, MRNA molecules, certain types of protein molecules, or all protein molecules from a cell lysate can be moieties to be isolated, manipulated or detected.

Non-limiting examples of cells include animal cells, plant cells, fingi, bacteria, recombinant cells or cultured cells. Animal, plant cells, fingus, bacterium cells to be isolated, manipulated or detected can be derived from any genus or subgenus of the Animalia, Plantae, fungus or bacterium kingdom. Cells derived from any genus or subgenus of ciliates, cellular slime molds, flagellates and microsporidia can also be isolated, manipulated or detected. Cells derived from birds such as chickens, vertebrates such fish and mammals such as mice, rats, rabbits, cats, dogs, pigs, cows, ox, sheep, goats, horses, monkeys and other non-human primates, and humans can be isolated, manipulated or detected by the present methods.

For animal cells, cells derived from a particular tissue or organ can be isolated, manipulated or detected. For example, connective, epithelium, muscle or nerve tissue cells can be isolated, manipulated or detected. Similarly, cells derived from an accessory organ of the eye, annulospiral organ, auditory organ, Chievitz organ, circumventricular organ, Corti organ, critical organ, enamel organ, end organ, external female genital organ, external male genital organ, floating organ, flower-spray organ of Ruffini, genital organ, Golgi tendon organ, gustatory organ, organ of hearing, internal female genital organ, internal male genital organ, intromittent organ, Jacobson organ, neurohemal organ, neurotendinous organ, olfactory organ, otolithic organ, ptotic organ, organ of Rosenmüller, sense organ, organ of smell, spiral organ, subcommissural organ, subfornical organ, supernumerary organ, tactile organ, target organ, organ of taste, organ of touch, urinary organ, vascular organ of lamina terminalis, vestibular organ, vestibulocochlear organ, vestigial organ, organ of vision, visual organ, vomeronasal organ, wandering organ, Weber organ and organ of Zuckerkandl can be isolated, manipulated or detected. Preferably, cells derived from an internal animal organ such as brain, lung, liver, spleen, bone marrow, thymus, heart, lymph, blood, bone, cartilage, pancreas, kidney, gall bladder, stomach, intestine, testis, ovary, uterus, rectum, nervous system, gland, internal blood vessels, etc can be isolated, manipulated or detected. Further, cells derived from any plants, fungi such as yeasts, bacteria such as eubacteria or archaebacteria can be isolated, manipulated or detected. Recombinant cells derived from any eucaryotic or prokaryotic sources such as animal, plant, fungus or bacterium cells can also be isolated, manipulated or detected. Cells from various types of body fluid such as blood, urine, saliva, bone marrow, sperm or other ascitic fluids, and subfractions thereof, e.g., serum or plasma, can also be isolated, manipulated or detected.

Isolatable, manipulatable or detectable cellular organelles include nucleus, mitochondria, chloroplasts, ribosomes, ERs, Golgi apparatuses, lysosomes, proteasomes, secretory vesicles, vacuoles or microsomes. Isolatable, manipulatable or detectable viruses include intact viruses or any viral structures, e.g., viral particles, in the virus life cycle that can be derived from viruses such as Class I viruses, Class II viruses, Class III viruses, Class IV viruses, Class V viruses or Class VI viruses.

Isolatable, manipulatable or detectable molecules can be inorganic molecules such as ions, organic molecules or a complex thereof. Non-limiting examples of ions include sodium, potassium, magnesium, calcium, chlorine, iron, copper, zinc, manganese, cobalt, iodine, molybdenum, vanadium, nickel, chromium, fluorine, silicon, tin, boron or arsenic ions. Non-limiting examples of organic molecules include amino acids, peptides, proteins, nucleosides, nucleotides, oligonucleotides, nucleic acids, vitamins, monosaccharides, oligosaccharides, carbohydrates, lipids or a complex thereof.

Any amino acids can be isolated, manipulated or detected by the present methods. For example, a D- and a L-amino-acid can be isolated, manipulated or detected. In addition, any building blocks of naturally occurring peptides and proteins including Ala (A), Arg (R), Asn (N), Asp (D), Cys (C), Gln (Q), Glu (E), Gly (G), His (H), Ile (I), Leu (L), Lys (K), Met (M), Phe (F), Pro (P) Ser (S), Thr (T), Trp (W), Tyr (Y) and Val (V) can be isolated, manipulated or detected.

Any proteins or peptides can be isolated, manipulated or detected by the present methods. For example, membrane proteins such as receptor proteins on cell membranes, enzymes, transport proteins such as ion channels and pumps, nutrient or storage proteins, contractile or motile proteins such as actins and myosins, structural proteins, defense protein or regulatory proteins such as antibodies, hormones and growth factors can be isolated, manipulated or detected. Proteineous or peptidic antigens can also be isolated, manipulated or detected.

Any nucleic acids, including single-, double and triple-stranded nucleic acids, can be isolated, manipulated or detected by the present methods. Examples of such nucleic acids include DNA, such as A-, B- or Z-form DNA, and RNA such as MRNA, tRNA and rRNA.

Any nucleosides can be isolated, manipulated or detected by the present methods. Examples of such nucleosides include adenosine, guanosine, cytidine, thymidine and uridine. Any nucleotides can be isolated, manipulated or detected by the present methods. Examples of such nucleotides include AMP, GMP, CMP, UMP, ADP, GDP, CDP, UDP, ATP, GTP, CTP, UTP, dAMP, dGMP, dCMP, dTMP, dADP, dGDP, dCDP, dTDP, dATP, dGTP, dCTP and dTTP.

Any vitamins can be isolated, manipulated or detected by the present methods. For example, water-soluble vitamins such as thiamine, riboflavin, nicotinic acid, pantothenic acid, pyridoxine, biotin, folate, vitamin $B_{12}$ and ascorbic acid can be isolated, manipulated or detected. Similarly, fat-soluble vitamins such as vitamin A, vitamin D, vitamin E, and vitamin K can be isolated, manipulated or detected.

Any monosaccharides, whether D- or L-monosaccharides and whether aldoses or ketoses, can be isolated, manipulated or detected by the present methods. Examples of monosaccharides include triose such as glyceraldehyde, tetroses such as erythrose and threose, pentoses such as ribose, arabinose, xylose, lyxose and ribulose, hexoses such as allose, altrose, glucose, mannose, gulose, idose, galactose, talose and fructose and heptose such as sedoheptulose.

Any lipids can be isolated, manipulated or detected by the present methods. Examples of lipids include triacylglycerols such as tristearin, tripalmitin and triolein, waxes, phosphoglycerides such as phosphatidylethanolamine, phosphatidylcholine, phosphatidylserine, phosphatidylinositol and cardiolipin, sphingolipids such as sphingomyelin, cerebrosides and gangliosides, sterols such as cholesterol and stigmasterol and sterol fatty acid esters. The fatty acids can be saturated fatty acids such as lauric acid, myristic acid, palmitic acid, stearic acid, arachidic acid and lignoceric acid, or can be unsaturated fatty acids such as palmitoleic acid, oleic acid, linoleic acid, linolenic acid and arachidonic acid.

D. Methods for Synthesizing a Library and Uses Thereof

In yet another aspect, the present invention is directed to a method for synthesizing a library, which method comprises: a) providing a plurality of microdevices, each of said microdevices comprises a substrate and a photorecognizable coding pattern on said substrate, wherein said photorecognizable coding pattern corresponds to an entity to be synthesized on said microdevice; and b) synthesizing said entities on said microdevices, wherein said microdevices are sorted after each synthesis cycle according to said photorecognizable coding patterns, whereby a library is synthesized, wherein each of said microdevices contains an entity that corresponds to a photorecognizable coding pattern on said microdevice and the sum of said microdevices collectively contains a plurality of entities that is predetermined before the library synthesis. Preferably, at least one of the microdevices used in the method does not comprise an anodized metal surface layer, e.g., an anodized aluminium surface layer. More preferably, at least 50% or all of the microdevices used in the method do not comprise an anodized metal surface layer, e.g., an anodized aluminium surface layer.

The microdevice used in the present method can comprise any suitable substrate. For example, the substrate can comprise silicon, e.g., silicon dioxide or silicon nitride, plastic, glass, ceramic, rubber, polymer and a combination thereof The substrate can comprises a surface that is hydrophobic or hydrophilic. The substrate can be in any suitable shape such as sphere, square, rectangle, triangle, circular disc, cube-like shape, cube, rectangular parallelepiped (cuboid), cone, cylinder, prism, pyramid, right circular cylinder and other regular or irregular shape. The substrate can be in any suitable dimension(s). For example, the thickness of the substrate can be from about 0.1 micron to about 500 microns. Preferably, the thickness of the substrate can be from about 1 micron to about 200 microns. More preferably, the thickness of the substrate can be from about 1 micron to about 50 microns. In a specific embodiment, the substrate is a rectangle having a surface area from about 10 squared-microns to about 1,000,000 squared-microns (e.g., 1,000 micron by 1,000 micron). In another specific embodiment, the substrate is a circular disc having a diameter from about 10 microns to about 500 microns. In still another specific embodiment, the substrate is in a cube-like shape having a side width from about 10 microns to about 100 microns. In yet another specific embodiment, the substrate is in an irregular shape having a single-dimension from about 1 micron to about 500 microns. In a preferred embodiment, the substrate is a composite comprising silicon, metal film and polymer film.

The microdevice used in the present method can comprise a photorecognizable coding pattern based on any suitable photorecognizable (optical) property constructed on the substrate. For example, the photorecognizable coding pattern can be photorecognizable (optical) property constructed on the material composition of the substrate itself, a hole in the substrate or a substance immobilized on the substrate, said substance having an optical refractive property that is different from the optical refractive property of the substrate. The versatility of the photorecognizable coding pattern can be caused by the shape, number, position distribution, optical refractive property, material composition, or a combination thereof, of the substrate, the hole(s), or the substance(s) immobilized on the substrate.

Although the microdevice used in the present method can comprise a single photorecognizable coding pattern, it can also be used in a high throughput synthesis and can comprise a plurality of photorecognizable coding pattern, e.g., a plurality of the holes and/or a plurality of the substances.

The photorecognizable coding pattern can be constructed on the substrate according to any methods known in the art. For example, the photorecognizable coding pattern can be fabricated or microfabricated on the substrate. Any suitable fabrication or microfabrication methods can be used including lithography such as photolithography, electron beam lithography and X-ray lithography (WO 96/39937 and U.S. Pat. Nos. 5,651,900, 5,893,974 and 5,660,680). If a substance having an optical refractive property that is different from the optical refractive property of the substrate is used as the photorecognizable coding pattern, the substance can be positioned, deposited or immobilized on the substrate by any suitable methods known in the art. For example, the substance can be positioned, deposited or immobilized on the substrate by any suitable methods such as evaporation or sputtering.

The substance can be positioned, deposited or immobilized on the substrate directly or via a linker, e.g., a cleavable linker. The substance can be positioned, deposited or immobilized on the substrate via a covalent or a non-covalent linkage. The substance can be positioned, deposited or immobilized on the substrate via a specific or a non-specific binding. Preferably, the linkage between the substance and the substrate can be a cleavable linkage such as a linkage cleavable by a chemical, physical or an enzymatic treatment.

The microdevice used in the present method can further comprise an element that facilitates and/or enables manipulation of the microdevice and/or a moiety/microdevice complex. Any suitable element can be used. For example, the element can be a cell, a cellular organelle, a virus, a microparticle, an aggregate or complex of molecules and an aggregate or complex thereof. The element can facilitate and/or enable manipulation of the microdevice and/or a moiety/microdevice complex by any suitable physical force such as a dielectrophoresis, a traveling-wave dielectrophoresis, a magnetic, an acoustic, an electrostatic, a mechanical, an optical radiation and a thermal convection force. For example, the element can be a magnetic material for manipulation by a magnetic force, a conductive or insulating material for manipulation by a dielectrophoresis force, a material with high or low acoustic impedance for manipulation by a acoustic force or a charged material for manipulation by an electrostatic force.

Although the microdevice used in the present method can comprise a single element, it can also be used in a high throughput analysis and can comprise a plurality of the elements, each of the elements facilitates and/or enables manipulation of the microdevice and/or the moiety/microdevice complex by a different physical force.

The microdevice used in the present method can further comprise a detectable marker or a molecular tag. Exemplary detectable markers include dye, radioactive substance and fluorescent substance. Exemplary detectable molecular tags include nucleic acid, oligonucleotide, protein and peptide sequences.

Any number of suitable entity(ies) can be synthesized on a single microdevice. For example, a single entity or a plurality of entities can be synthesized on a single microdevice. Preferably, a single entity is synthesized on a single microdevice.

The present method can be used to synthesize any kind of library. For example, the synthesized entities can be peptides, proteins, oligonucleotides, nucleic acids, vitamins, oligosaccharides, carbohydrates, lipids, small molecules, or a complex or combination thereof. Preferably, the synthesized library comprises a defined set of entities that are involved in a biological pathway, belongs to a group of entities with identical or similar biological finction, expressed in a stage of cell cycle, expressed in a cell type, expressed in a tissue type, expressed in an organ type, expressed in a developmental stage, entities whose expression and/or activity are altered in a disease or disorder type or stage, or entities whose expression and/or activity are altered by drug or other treatments.

In a specific embodiment, the synthesized library comprises a defined set of nucleic acid, e.g., DNA or RNA, fragments such as a defined set of nucleic acid fragments that cover an entire genome, e.g., the entire human genome sequence. Preferably, each of the nucleic acid fragments in the synthesized library comprises at least 10, 15, 20, 25, 50, 75, 100, 200, or 500 nucleotides .

In another specific embodiment, the synthesized library comprises a defined set of protein or peptide fragments such as a defined set of protein or peptide fragments that cover protein or peptide sequences encoded by an entire genome, e.g., the entire human genome sequence. Preferably, each of the protein or peptide fragments in the synthesized library comprises at least 5, 10, 15, 20, 25, 50, 75, 100, 150, 200, 300, 400 or 500 amino acid residues.

In still another specific embodiment, a library that is synthesized according to the above-described method is provided.

In yet another specific embodiment, a method for generating an antibody library is provided, which method comprises: a) contacting a library synthesized by the above-described method with a plurality of antibodies; and b) selecting and/or recovering the antibodies that specifically bind to the entities of the library synthesized according to the above-described method. Any suitable antibodies can be used in the present method. For example, plurality of antibodies used in the present method is a phage display library (See U.S. Pat. Nos. 6,127,132 and 6,174,708).

E. The Microfabricated Two-dimensional Optical Encoders and Their Uses

In yet another aspect, the present invention is directed to an example of a microdevice of the present invention, a two-dimensional optical encoder and uses thereof.

In a specific embodiment, the present invention is directed to a two-dimensional optical encoder, which encoder comprises: a) a substrate; and b) a microfabricated or micromachined two-dimensional optical code on said substrate. Preferably, the two-dimensional optical encoder does not comprise an anodized metal surface layer, e.g. an anodized aluminium surface layer.

Any suitable material can be used in the substrate. Preferably, the substrate comprises silicon, silicon dioxide, glass, plastic, polymer, magnetic material, carbon, metal, oxidized metal or a composite thereof.

Any suitable pattern or substance or composites can be used as the two-dimensional code. Preferably, the two-dimensional code is a grating, an aperture-based code or a black-white line-segment code.

In another specific embodiment, the present invention is directed to a carrier for chemical synthesis, which carrier comprises a surface suitable for chemical synthesis, said surface comprises a microfabricated or micromachined two-dimensional optical code, and said optical code identifies a chemical reaction to be conducted on said surface and/or product of said chemical reaction. Preferably, the carrier does not comprise an anodized metal surface layer, e.g., an anodized aluminium surface layer.

The carrier can have any suitable shape. For example, the carrier can be a cube, a rectangular parallelepiped (cuboid), a cone, a cylinder, a prism, a pyramid and a right-angled circular cylinder. Preferably, the carrier does not comprise an anodized metal surface layer, e.g., an anodized aluminium surface layer. The carrier can comprise a spherical portion and a flat portion, wherein said flat portion comprises a microfabricated or micromachined two-dimensional optical code and said spherical portion is used for chemical synthesis. Also preferably, the non-coding region of the carrier can further comprises a chemical layer linked to the carrier surface via a cleavable linker, e.g., an optically cleavable, an enzymatically cleavable and/or a thermally cleavable linker, and said cleavable linker allows for subsequent chemical synthesis reactions.

In still another specific embodiment, the present invention is directed to a carrier for labeling a substance, which carrier comprises a surface for binding or linking a substance, and a microfabricated or micromachined two-dimensional optical code on said surface, said optical code is used for identifying said substance linked or coupled to said carrier. The carrier can have any suitable shape. For example, the carrier can be a cube, a rectangular parallelepiped (cuboid), a cone, a cylinder, a prism, a pyramid and a right-angled circular cylinder. Preferably, the carrier comprises a spherical portion and a flat portion, wherein said flat portion comprises a microfabricated or micromachined two-dimensional optical code and said spherical portion is used for linking or coupling the substance.

In still another specific embodiment, the present invention is directed to a method for conducting chemical synthesis on the above-described two-dimensional optical encoder, which method comprises, based on optical code on said encoder, introducing said encoder into a corresponding reaction chamber and allowing a predetermined chemical synthesis reaction to be conducted on said encoder. Preferably, the method further comprises the following steps: a) mixing a plurality of the two-dimensional optical encoders, each encoder having a unique optical code representing the corresponding synthesis reaction(s) to be conducted and/or product(s) to be synthesized on said encoder; b) chemically modifying the non-encoding regions of the surface of the encoders; c) continuously passing the optical encoders through a sorting device capable of identifying the optical code on said optical encoders, and transporting or sorting the optical encoders into corresponding reaction chambers based on their optical codes; d) performing the chemical synthesis procedures on said optical encoders in their corresponding reaction chambers; and e) after each step of the chemical synthesis, mixing the optical encoders and sorting the encoders in a sorting device into new, corresponding reaction chambers again based on the optical codes on said encoders and the subsequent requisite synthesis steps for said encoders, performing a new step of the chemical synthesis until all requisite synthesis steps are performed.

The sorting device used in the method can comprise a microchannel that allows the passage of one and only one optical encoder at a time. The encoder suspended in a liquid solution is manipulated or controlled to pass through the microchannel via an applied force, and the encoder is monitored or detected by a code-reader that is located in the vicinity of the microchannel.

Any suitable physical force can be used in the present method. For example, the applied force on the optical encoder, or substances linked thereto, can be a traveling-wave dielectrophoresis force, a traveling-wave magnetic field-force or a traveling-wave acoustic wave-induced force, whereby said applied force causes the encoders to pass through the microchannel and be sorted. In another example, the applied force on the optical encoder, or substances linked thereto, can be an electroosmotic pumping force, a mechanical pumping force and/or an electrohydrodynamic pumping force, said applied forces are applied to the solution liquid of the reaction system, and said solution liquid carries the optical encoder and the linked substances through the microchannel.

After the identification of the optical codes on the optical encoders via the sorting device, the encoders can be transported, based on the optical code signals that are read-out from the encoder, to different reaction chambers that are linked to the microchannels.

In yet another specific embodiment, the present invention is directed to a chip, which chip comprises a plurality of the above microfabricated two-dimensional optical encoders, each encoder having biological and chemical substance(s) linked thereto, and said biological and chemical substance(s) are capable of being identified by the optical code on each optical encoder. Preferably, at least one of the optical encoders used in the chip does not comprise an anodized metal surface layer, e.g., an anodized aluminium surface layer. More preferably, at least 50% or all of the optical encoders used in the chip do not comprise an anodized metal surface layer, e.g., an anodized aluminium surface layer.

Any biological and chemical substance(s) can be linked to the present chips. For example, DNA, RNA, peptide, protein, antibody, antigen, sugar, lipid, cytokine, hormone, cell, bacteria, virus and a composite thereof can be linked to the present chips.

In yet another specific embodiment, the present invention is directed to a method for measuring and/or detecting a substance, which method comprises: a) labeling a substance to be measured and/or detected; b) providing a plurality of the above chips, each of said chips having immobilized thereto a different biological or chemical entity and the identity of said entity corresponding to the optical code of said chip; c) binding and/or reacting the labeled substance with said plurality of chips provided in step b); d) conducting a wash to remove substances that do not bind and/or react with said entities on said chips; e) passing said washed chips sequentially through a device to detect and measuring labels of said substances attached to said chips and to decode the code on the chip, thereby measuring and/or detecting the type or quantities of said substances.

In exemplary embodiments, the present invention discloses a large-scale chemical synthesis control method. In this method, the 2-D optical encoders serve as carriers. Based on the code on the 2-D optical encoders, these encoders are manipulated and transported to different reaction chambers for different synthesis reactions.

Preferably, the large-scale chemical synthesis control method includes:

1) using different optical codes to denote the different synthesis reactions and related production. Mixing the different 2-D optical encoders and modifying the surface;

2) using a sorting device to readout the codes on the 2-D optical encoders, then based on the first code on the encoders, transporting these encoders to related reaction chambers;

3) after the reaction cycle is complete, mixing all 2-D optical encoders and then using sorting device to sort again. Based on the second code on the encoders, transporting these encoders to related reaction chambers; and 4) repeating step 3, each time reading the next code on the encoders, until finishing all the synthesis reaction.

Alternatively, each optical encoder can contain an intact code which identifies the entire synthesis steps/procedures and the product to be synthesized on that particular optical encoder. This way, it is not necessary to decode each digit of a code after each synthesis cycle.

Here, the sorting device has a small channel. Each time only one encoder in the solution can be manipulated to go through the channel. At the same time, the readout system will read the code on the 2-D optical encoder and decode it.

The applied forces for manipulating the 2-D optical encoders or the linked substances include, but are not limit to, electric force, magnetic force, acoustic force and mechanical force. These applied forces can control and manipulate the 2-D optical encoders and the linked substances in the solution and make sure each time only one encoder in the solution can go through the channel.

After the readout system in the sorting device decodes the code on the 2-D optical encoder, the 2-D optical encoders are transported to different reaction chambers. Each time based on the different decoding signal, the sorting device can connect the related reaction chamber with the microchannel and let the 2-D optical encoder go into the chamber for next synthesis reaction.

The present invention also discloses a chip. This chip includes many microfabricated 2-D optical encoders. Each 2-D optical encoder can bind with one kind of biological substance or chemical substance, also the code on each 2-D optical encoder can specifically denote the biological material or chemical material which binds to this 2-D optical encoder. The non-coded surface region of the 2-D optical encoder can be modified with functional layer for biological material or chemical material binding.

In this chip application, the biological substances include, but are not limited to, DNA, RNA, peptide, protein, antigen, antibody, monosaccharide, oligosaccharide, carbohydrate, lipid, hormone and the complex thereof, cell, virus and so on. A common format for the biological material or chemical material is a probe used in the chip.

The present invention also discloses a method using the present chip to detect different substances in a sample. This method includes:

1) labeling the "unknown" substances in a sample;

2) providing 2-D optical encoders, wherein each 2-D optical encoder binds with one kind of biological substance or chemical substance, and the code on each 2-D optical encoder can specifically denote the bound biological material or chemical material;

3) mixing the 2-D optical encoders and reacting them with "unknown" substances in the sample; and 4) after the reaction, manipulating and transporting these 2-D optical encoders to a readout system one by one. When a 2-D optical encoder with labeled substance goes through the readout system, the labeled substance will trigger the readout system and the readout system will read and decode the code on this 2-D optical encoder. Then the class and quantity of the "unknown" material binding on the 2-D optical encoder surface will be ascertained.

The label for "unknown" substances includes, but are not limited to, fluorescence label, isotope label, etc.

In this present detection method, since 2-D optical encoders serve as the carriers for biological substances or chemical substances, it is easy to determine the identity and quantity of unknown substances and also it is easy to conduct the high throughput screening for reaction products.

The present 2-D optical encoders can be used in a wide variety of fields such as chemistry, pharmaceutical industry and biotechnology.

Figure 14:
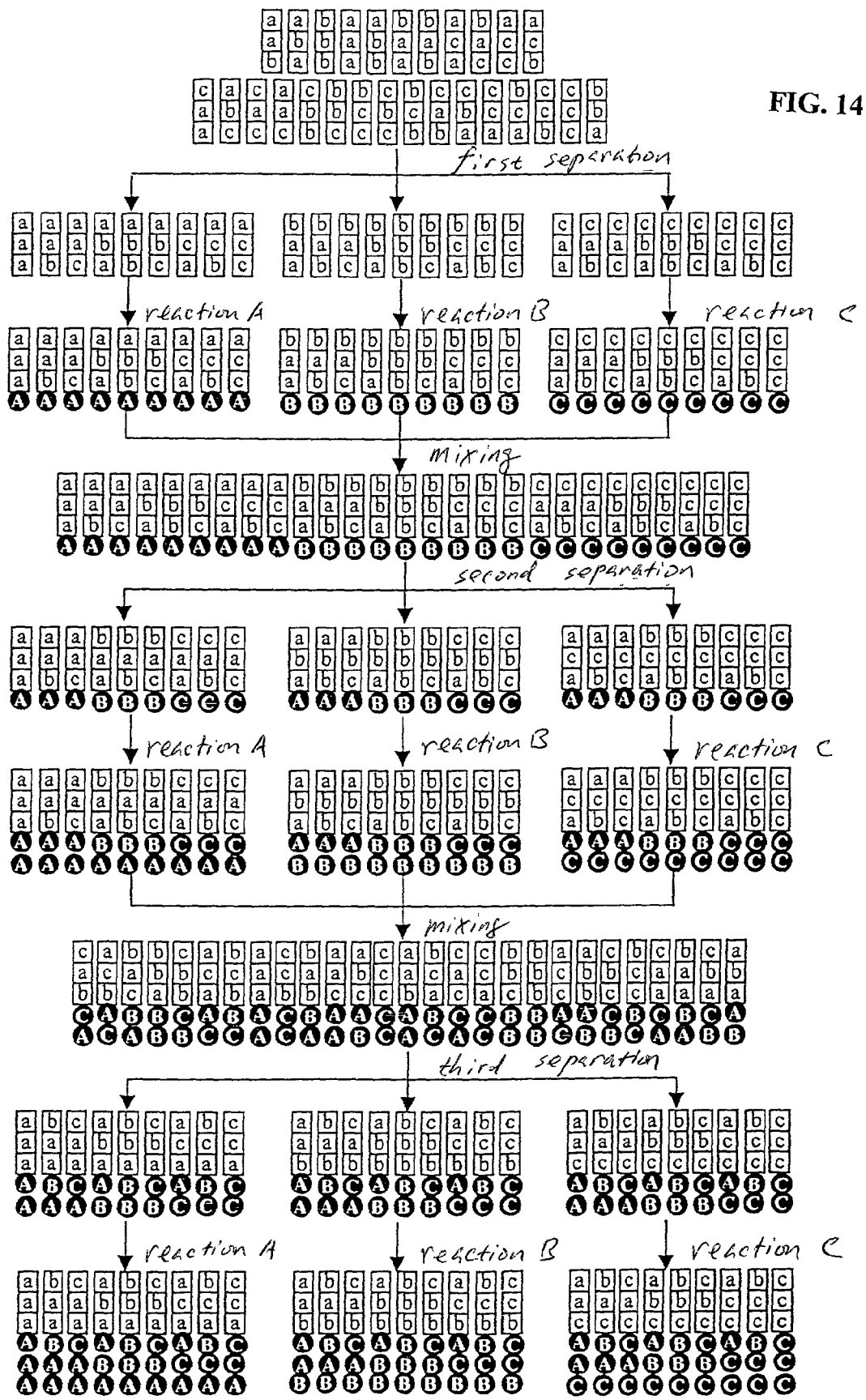
FIG. 14 is a schematic diagram showing chemical synthesis process using 2-D optical encoders, an exemplary microdevice of the present invention.

Since each kind of 2-D optical encoder has a specific code that can distinguish it from other 2-D optical encoders, 2-D optical encoders can be used to label and control the compound synthesis process. FIG. 14 is the schematic diagram showing the synthesis process for different compounds using 2-D optical encoders. For example, using three different 2-D optical encoders (M1, M2 and M3) to synthesis three different compounds: compound W1 (a-b-c), compound W2 (a-c-c), and compound W3 (b-a-c). Here a, b, c are different products coming from different synthesis reactions. The code for 2-D optical encoder M1 is 123, for 2-D optical encoder M2 is 133, for 2-D optical encoder M3 is 213. Code 1 defines synthesis reaction a, code 2 defines synthesis reaction b, and code 3 defines synthesis reaction c. These three different kinds of 2-D optical encoders are mixed in one chamber. After modifying the surfaces of these 2-D optical encoders, the cleavable linkers are bound to the encoder surface. These cleavable linkers include, but are not limited to, optically cleavable linker, enzymatically cleavable linker, and thermally cleavable linker, etc. The following synthesis reactions are conducted on these linkers and the reaction products are connected to these linkers. Then the sorting device is used to sort these 2-D optical encoders. Based on the codes on these 2-D optical encoders, the 2-D optical encoders are transported to related reaction chambers. For example, at the first sorting process, the sorting device decodes the first code on the 2-D optical encoder. 2-D optical encoders M1 and M2 are transported to chamber a to carry out synthesis reaction a. 2-D optical encoder M3 is transported to chamber b to carry out synthesis reaction b. After finishing the first-round synthesis reaction, all the 2-D optical encoders are mixed and then sorted again. Based on the second code on the 2-D optical encoders, 2-D optical encoder M3 is transported to chamber a to carry out synthesis reaction a. 2-D optical encoder M1 is transported to chamber b to carry out synthesis reaction b and 2-D optical encoder M2 is transported to chamber c to carry out synthesis reaction c. Following this rule, after complete of each synthesis reaction, all the 2-D optical encoders are mixed again. Then based on the related code on these 2-D optical encoders, the sorting device can transport them to related chambers to carry out related synthesis reactions. When all the synthesis reaction are completed, the desired compounds are linked to 2-D optical encoders. Through reading the codes on these 2-D optical encoders, it is easy to know the identity of the compounds. Also these compounds are linked to 2-D optical encoders by cleavable linkers so that it is easy to recover the compounds.

In FIG. 14, each rectangle with three letters (a, b and c) is a 2-D optical encoder. Here the letters are the codes for 2-D optical encoder. The capital letter in the black circle denotes the production of related synthesis reaction.

Figure 15:
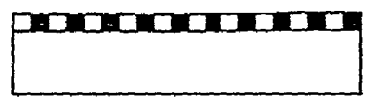
FIG. 15 illustrates three different coding methods for 2-D optical encoders.
Figure 15:
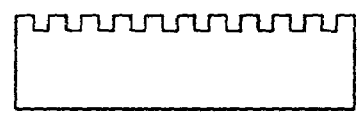
Figure 15:

In FIG. 15, there are three different optical coding methods. FIG. 15(A) illustrates bar codes. FIG. 15(B) illustrates grating codes. FIG. 15(C) illustrates hole codes.

Figure 16:
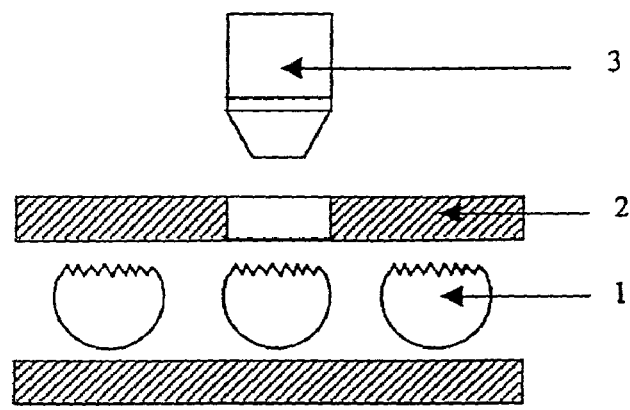
FIG. 16 is a schematic diagram showing sorting and analyzing of the 2-D optical encoder.

FIG. 16 illustrates sorting of a sector sphere encoder 1, i.e., an encoder having a spherical portion and a flat portion. The codes are located on the flat surface of this sector sphere. And the other surface of this sector sphere contains the substrate for compound synthesis. The density of this kind of 2-D optical encoder is nearly the same as the solution. So the 2-D optical encoder can float in solution and the flat surface of this 2-D optical encoder will always face up. The sorting device has a microchannel 2 and each time only one 2-D optical encoder can go through this microchannel 2. A readout system 3 is located around the microchannel 2. When the sorting device sorts the mixed 2-D optical encoders, the 2-D optical encoders in the solution will go through the microchannel 2 quickly. The readout system 3 will read and decode the code on each 2-D optical encoder. And then the 2-D optical encoders are transported to different reaction chambers behind the sorting device. Each time based on the different decoding signal; the sorting device can connect the related reaction chamber with the microchannel 2 and let the 2-D optical encoder go into the chamber for next synthesis reaction.

The carrier or 2-D optical encoder showed in FIG. 16 can be of any suitable shape such as a cube, a rectangular parallelepiped (cuboid), a cone, a cylinder, a prism, a pyramid and a right-angled circular cylinder. The applied forces for manipulating the 2-D optical encoders or the linked substances include, but are not limit to, electric forces, magnetic forces, acoustic forces and mechanic forces. These applied forces can control and manipulate the 2-D optical encoders or the substances on these encoders in the solution and make sure each time only one encoder in the solution can go through the microchannel 2 in the sorting device. Also applied forces can be selected from electroosmotic pumping forces, mechanical pumping forces, and electrohydrodynamic pumping forces. These applied forces are applied to the solution liquid of the reaction system, and the solution liquid will carry the 2-D optical encoders and the linked substances through the microchannel on sorting device.

The present 2-D optical encoders also can be used to make different kinds of chips, such as DNA chip, protein chip and polysaccharide chips.

The 2-D optical encoders can be used to fabricate a chip, e.g., a biochip. First, many kinds of different 2-D optical encoders 1 can be prepared. These 2-D optical encoders have a modified finctional layer linked to the non-coding surface region. And the functional layer is used for immobilizing the biological or chemical substances. Examples of the functional layer include, but are not limited to, a molecular monolayer, a membrane, a gel, a porous or non-porous material layer. The functional layer may be an additional layer adhered to the surface of 2-D optical encoder (through microfabrication method). Alternatively, the functional layer may be formed by direct chemical-modification of the surface molecules of the 2-D optical encoder. Preferably, the functional layer should have minimal or no non-specific bindings to molecules other than ligand molecules, and should allow efficient binding or attachment of the necessary biological substances or chemical substances. The functional layer may be a hydrophilic or hydrophobic molecular monolayer, a hydrophilic or hydrophobic membrane, a hydrophilic or hydrophobic gel, a polymer layer, porous or non-porous materials and/or the composite of these materials. Molecular monolayer refers to single molecular layer (for example, Langmuir-Blodgett film). For immobilizing nucleic acid probes, binding materials such as nitrocellulose or nylon may be used as in Southern or northern blots. Proteins and peptides can be bound by various physical (e.g., hydrophobic) or chemical approaches. For example, specific receptors such as antibodies or lectins can be incorporated into the functional layer for binding target molecules of protein or peptide-types. Depending on the intended targets and the assays or reactions to be carried out by the biochip, different molecules can be incorporated into the functional layer for binding target molecules. These molecules incorporated in the functional layer for binding target molecules are referred to as the functional groups. Examples of the functional groups include, but are not limited to, aldehydes, carbodiimides, succinimydyl esters, antibodies, receptors, and lectins. The functional groups also include chemical groups or molecular sites that are formed through chemical modification on the 2-D optical encoder surface molecules.

For example the 2-D optical encoder can be used in the fabrication of a protein chip. Each kind of proteins as probes will be immobilized on the functional layer of different kinds of 2-D optical encoders. The codes of the 2-D optical encoders will specifically denote the proteins immobilized on the 2-D optical encoders. So the classes of the protein immobilized on the 2-D optical encoders can be easily identified through decoding the code on the 2-D optical encoder. These 2-D optical encoders can be used to detect the "unknown" protein. First, the "unknown" proteins in the sample solution are labeled with fluorescence. Then a plurality of 2-D encoders with different substances are loaded and reacted with "unknown" proteins. After the stringency control wash, these 2-D optical encoders are manipulated to go through the detection system one by one.

Figure 17:
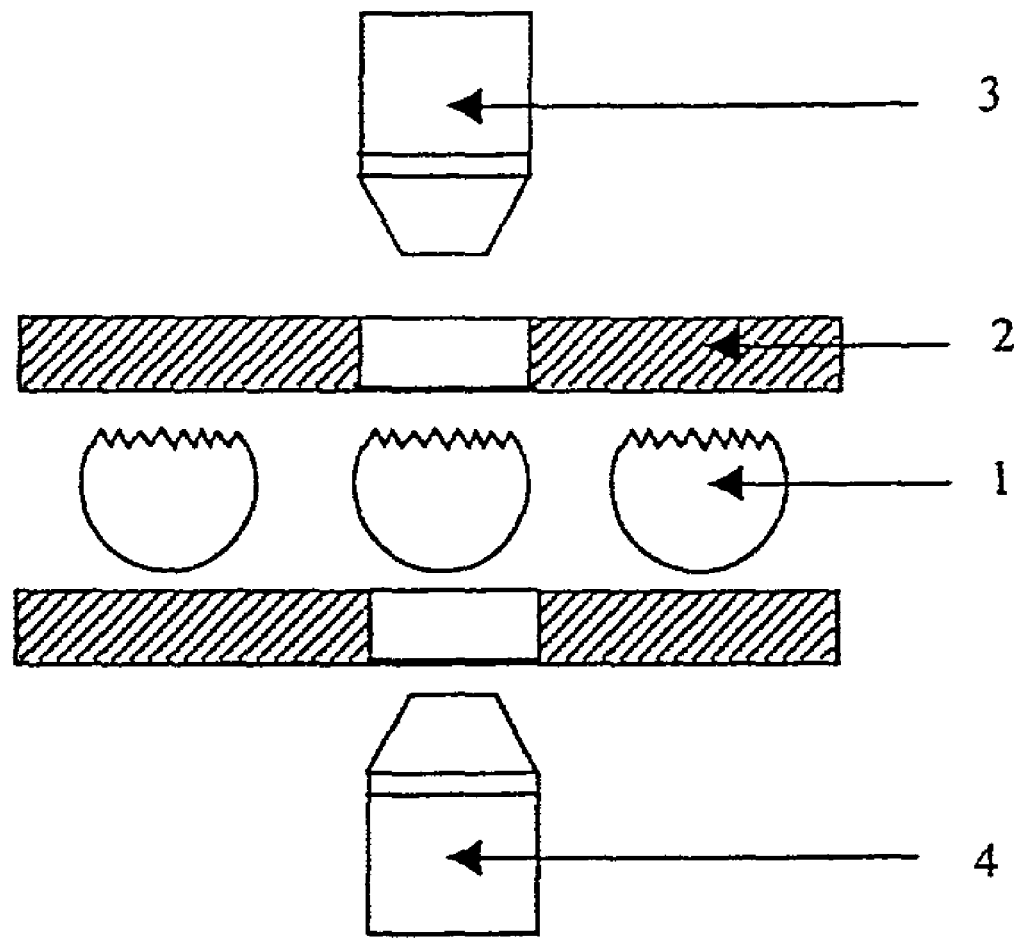
FIG. 17 is a schematic diagram showing a process using 2-D optical encoders to detect "unknown" substances.

FIG. 17 is a schematic diagram showing an exemplary detection system of the present invention. This detection system is similar to sorting device shown in FIG. 16. The detection system has a microchannel 2. The dimension of this microchannel 2 is fit for 2-D optical encoders. That means each time only one 2-D optical encoder can go through this microchannel. The forces induced by various effects such as traveling-wave dielectrophoresis, traveling-wave magnetic field, traveling-wave acoustic wave, mechanic force induced by fluid motion, etc., can control and manipulate the 2-D optical encoders or the substances on these encoders in the solution and make sure each time only one encoder in the solution can go through the microchannel 2 in the detection system. Also applied forces can be selected from various pumping forces such as electroosmotic pumping forces, mechanical pumping forces, and electrohydrodynamic pumping forces. These forces are applied to the solution liquid of the reaction system, and the solution liquid will carry the 2-D optical encoders and the linked substances through the microchannel on sorting device. There are two windows on the same location of the microchannel. Above the up window there is a readout system 3 and below the bottom window there is a fluorescence detection system 4. When the 2-D optical encoder goes through the microchannel 2, if there is "unknown" protein from a sample binding with the protein probe immobilized on the 2-D optical encoder, the fluorescence detection system 4 will detect the fluorescence signal and trig the readout system 3 to read and decode the code on this 2-D optical encoder. Then based on the decoding result, the class of "unknown" protein may be ascertained. The fluorescent signal detected by the detection system 4 can also be used to determine the quantity of the protein in the sample.

The advantage of this kind of biochip is that users can immobilize different kinds of probe, e.g., proteins probes, to different microfabricated 2-D optical encoders by themselves. So it is easy for users to construct different probe libraries.

To measure and detect the "unknown" substance in a sample, the "unknown" substance molecules may be labeled with fluorescence or isotope. After the reaction, the 2-D optical encoders will go through the detection system one by one. The detection system will ascertain if there is reaction between the probe on the 2-D optical encoder with the "unknown" substance molecules and determine the class of this 2-D optical encoder. The signals detected in the detection systems 3 and 4 can be used, alone or in combination, to determine the presence, absence or amount of an analyte, e.g., a target protein, in the sample.

F. EXAMPLES

1. Information Encoded Fluid Suspendable Microdevice

In one specific embodiment, the invention is intended to solve the problems encountered in 2-dimensional micro array systems as well as 3-D micro particle systems. The invention described herein is a system compromising a microdevice, individual microdevices that are information encoded, a detection system and a data analysis system. It may also include an array system for application of biological samples.

The microdevice can be encoded individually using a bar coding system. Each individual encoded microdevice serves as a biological reaction and detection platform. The microdevice can be square or circle or other shape. Its dimension can be 50 micrometer by 50 micrometer (10 micron to 100 micron). The microdevice can be thin, e.g., about 100 anstrong to about 1 micron. It can be biologically compatible and liquid suspensable. The microdevice can be used in studies of nucleic acid, protein, biochemical reaction, cell biology, diagnostics and drug screen.

The microbiochip system can comprise or consist of (a) individually encoded microdevices, (b) devices that separate the microdevices, (c) a detection system that reads both coding information and reaction information and (d) a data processing system.

The microdevice can be encoded by a pattern that is located on the chip. The pattern can be created by making an array of photo transmissible micro sized holes or by dotted reflection materials. The processes producing those patterns can be conducted through fabrication called chemical etching. A series of masks that have different patterns can be created by computers and produced by conventional technology. Thin films of inert materials, e.g., silicon, glass, metal, ceramic, plastic, etc., can be laid on top of a flat polymer surface, such as agarose for chemical etching. Photolithography process can be carried out. After the desired pattern has been created to produce the patterns of the film, the polymer layer at the bottom can be removed by the appropriate method. In the case of agarose, heat is needed to melt the agarose and release individual microdevices. The size of the microdevices can be about less than 50, 50-100, or more than 100 µm in diameters and can be circle, square, rectangle or any other shape. The information holes or spots on the microdevice may be numbered. The microdevice can be modified by chemical process to obtain desired surface chemistry suitable for biological reactions.

After the microdevices have reacted with biochemical analytes the microdevices can be separated by a microdevice separation chamber. In this chamber, microdevices in solution can be isolated and separated in a narrow thin micro channel and lined up one by one in the channel. Then the individual microdevice can be transported to a detection zone for analysis of the coding information and reaction information.

The detection system can comprise or consist of an optical detector, an analyte detector, e.g., a fluorescence detector and data analysis software. The optical detector will detect the light transmission pattern of the individual microdevice to decode the encoded information. The fluorescence detector will detect the fluorescence signal generated from an analyte specific reaction. Data analysis software will analyze the data and provide two types of information. One is the identity of the specific analyte on a microdevice, such as a specific nucleic acid probe, antibody, specific protein or other moiety of interest, such as a cell, a bacterium, and a virus. The system will also provide qualitative and quantitative information regarding the specific analyte on a microdevice.

The system can be used for many purposes such as analyzing nucleic acid hybridization, antibody-antigen interactions, receptor-ligand interactions, cell sorting, screening of phage particles that display antibody or binding partners of interest. The system can also be used for screening hybridoma cells that carry specific antibody, chemical compound synthesis and screening and studying other molecular interaction events.

2. Microfabricated Encoding Microparticles for Microfluidic and Biochip Applications In another specific embodiment, the invention concerns information encoded microparticles and uses thereof. The microparticles or microdevices are microfabricated structures or the microdevices disclosed in the present invention. The structures or microdevices may be a thin, rectangular shaped substrate (e.g. thickness between <1 micron to >10 micron with major surface areas between <10 squared-micron and >10,000 squared-microns). Or, the structures may be thin, circular disks (e.g. thickness between <1 micron to >10 micron with circle-type surface having diameter between <10 microns and >500 microns). Or, the structures may have cube-like shapes (side width between <10 and >100 micron). Or, the microstructures may have other irregular shapes. The single-dimensions of the structures may vary between as small as <1 micron and as large as >500 micron. The microfabricated structures or the microdevices may be from simple material types such as silicon, plastic, ceramics, metals, or the structures may be made from composite materials comprising silicon, metal film and polymer films.

Preferably, the microfabricated structures or the microdevices have encoding patterns on the surface or on the body. The encoding patterns would allow, first of all, many types of fabricated structures to be made, and secondly, the discrimination and distinguishing between different microstructures. There may be a number of methods for incorporating encoding patterns on the structures. One approach is to incorporate "holes" on the chip surfaces. For example, on rectangular chips having dimensions of 1 by 5 by 50 microns. Along 50 micron dimensions, there may be 4 holes, spaced 10 microns apart for the center-to-center distance. The holes may have a diameter of 2 microns. Depending on whether holes are produced at the particular positions and depending on how many holes there are on the microstructures or microdevices, there are total 16 combinations ($=2^4$). FIG. 1 provides encoding examples of microstructures or microdevices where the structures are rectangular shape and the holes are introduced along the middle lines of the structures.

Figure 2:
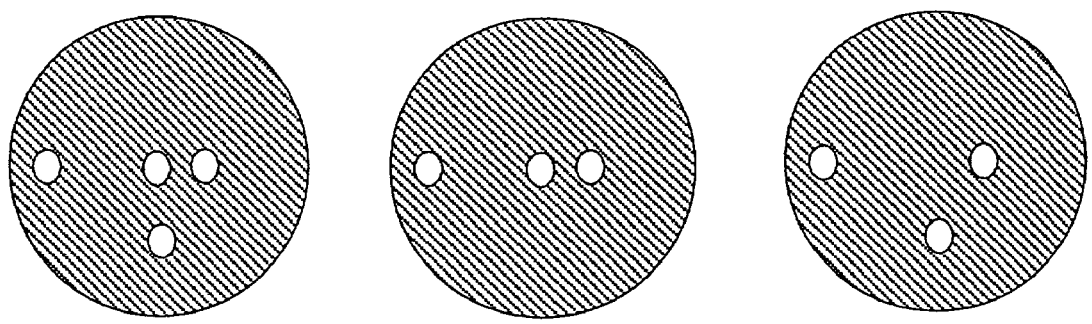
FIG. 2 illustrates another example of the microdevices (microstructures) wherein the microdevices are in circular disc shape on which holes are produced.
Figure 3:
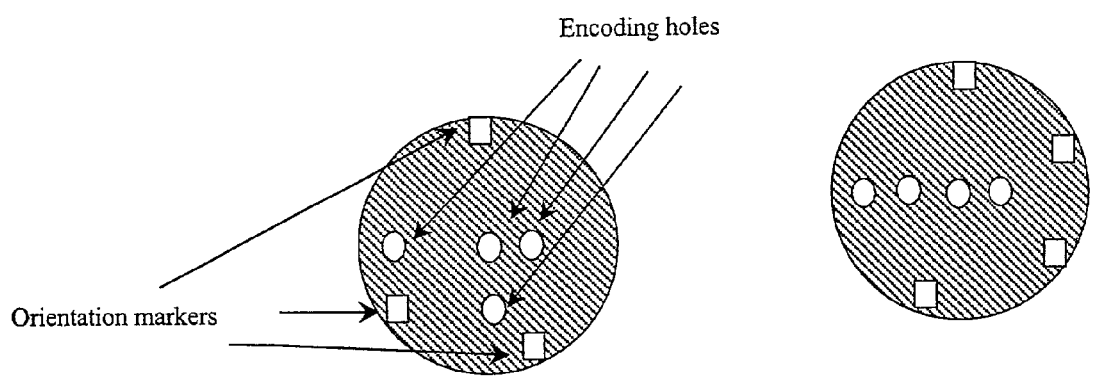
FIG. 3 illustrates another example of the microdevices (microstructures) wherein the microdevices are in circular disc shape on which holes are produced and on which orientation/alignment markers are also fabricated.

Another example of the microstructures or the microdevices is the circular discs on which holes are produced. Possible examples are shown in FIG. 2 where the holes are positioned not symmetrical on the circular disk. The holes are located at four different diameter positions ($r=0$ at the center, $r=\frac{1}{4}$*radius; $r=\frac{1}{2}$*radius; $r=\frac{3}{4}$*radius). Again there will be 16 encoding combinations—leading to total 16 kinds of microfabricated structures or microdevices. FIG. 2 shows three examples of such encoding discs. FIG. 3 shows an example of the microfabricated microdevices. The circular holes on the disk are used as the encoding pattern. The rectangular holes on the edges of the disks are used as orientation markers. During the decoding step, these orientation markers can be detected, and the relative positions (and the numbers) of the circular holes with regard to these orientation markers can be analyzed to decode the encoding patterns on the microdevices.

Holes are just one example for making encoding structures or encoding microdevices. Materials of different optical refractive properties may also be used. For example, encoding structures may be fabricated on silicon wafers whilst encoding, small circle-type disks are made of a metallic material such as aluminum, silver or gold. As long as the encoding pattern on the structures can be read through some mechanism, the structures or microdevices can be utilized as encoding devices. As long as the structures may be fabricated through certain fabrication procedures and encoding patterns and features are incorporated on the structures, such structures may be used for the purpose of encoding for different types of the structures or microdevices.

Preferably, in use, these microdevices would have certain surface chemical properties that would allow them to bind to some bioanalytes (e.g., cells, DNA, RNA, proteins). For example, the microdevice surface may have antibodies immobilized so that proteins can bind to the microdevice surface. In another example, the microdevice surface may have single stranded DNA attached so that the single-stranded DNA may then bind to its complementary strand. In such cases, the microdevices will be used as binding partners for a number of moieties to be manipulated (see the co-pending U.S. patent application Ser. No. 09/636,104, filed Aug. 10, 2000). These microdevices can be used for capturing target cells, binding to target protein, binding to target DNA segments, binding to target RNA segments, or reacting with any type of bioanalyte from a mixture solution.

For example, we could have two types of encoding microdevices—one is labeled with antibodies (Abs) for T-lymphocyte (microdevice one) and another type labeled with Abs for B-lymphocytes (microdevice two). These microdevices will be incubated with a blood sample or diluted blood sample. The microdevices may then bind to T-cells and B-cells separately. We can then use certain methods to isolate these target cell-microdevice complexes (there are two types, the first type is T-cell with microdevice one, the second type is B-cell with microdevice two) from the total cell mixture. We can then use certain methods to identify the microdevices and sort the cell-microdevice mixture.

In another example, we have 100 types of encoding microdevices—each is labeled with one type of Ab against certain target proteins. Incubating such microdevices with a protein mixture solution may result in the target protein molecule coupling to the surface of the encoding microdevices. We can then use fluorescently labeled secondary antibodies to label the bound proteins. We then can measure the fluorescent levels on each microdevice and simultaneously, and determine which he identity of each microdevice. We then establish the type of microdevices tested and fluorescent levels on the microdevices. This would provide information as to the identity and amount or concentration target proteins in the test solution.

In the above example, the fabricated microdevices or the fabricated microdevices are used in the same way as multiple microbeads that have been developed for assaying and analyzing bioanalytes in mixture solutions.

Preferably, the fabricated microdevices or the microdevices have desired physical properties such that these physical properties allow these microdevices to be manipulatable by on-chip generated physical forces. For example, if dielectrophoresis is used to control and manipulate microdevices, the microdevices should have certain dielectric properties so that their properties are different from those of the solution in which the microdevices are introduced or suspended. In such cases, dielectrophoresis theories may be applied to design the materials, sizes, geometries and compositions of such microfabricated microdevices. In another example, if magnetophoresis with magnetic fields is used to move and manipulate the fabricated microdevices, then the microdevices are expected to have desired magnetic properties, e.g., magnetic film materials have been introduced into the microdevices.

Microfabricated encoding microdevices or microdevices can be fabricated or micromachined with a number of standard procedures. Photolithographic processes may be used with masks that have defined patterns. These patterns will correspond to the final encoding patterns. The steps involved may include steps like deposition of thin film layers, etching off the thin film at designated places etc. A number of articles that described certain fabrication methods that may be used for producing such microfabricated microdevices are incorporated by reference (e.g., "Design of asynchronous dielectric micromortors", by Hagedom et al., J. Elecetrostatics, Volume 33: 159-185, 1994; "Design considerations for micromachined electric actuators", by Bart et al., Sensors and Acuators, Volume 14: 269-292, 1988). Appropriate materials with desired physical properties should be used so that microfabricated microdevices may be moved or manipulated or controlled by certain physical forces generated by physical fields. The free standing microdevices after fabrication will then be modified on their surfaces so these microdevices could bind to the surfaces of the microdevices.

The microfabricated encoding microdevices or the devices are then chemically or biochemically modified. Common procedures that are used for modifying solid substrates may be utilized for such purposes. The modification steps will lead to specific molecules attached on the microdevices' surfaces. These specific molecules may include antibodies, DNAs, RNAs, ligands, enzymes etc. In such cases, these molecules are used as binding partners.

These microfabricated encoding microdevices having specific molecules attached to their surfaces may then be used to bind the target bioanalytes from a solution mixture. After binding to the target analytes, the target analytes may then be further detected on these microdevices. For example, individual microdevices can be detected by determining their types and sorting them out according to their individual types using, e.g., biochip-based devices—so that each type of microfabricated microdevices is concentrated or accumulated into one specific region on a biochip. Then the target molecules on these microdevices are further labeled and detected. The labeling may use or involve fluorescent molecules. Detection may then be based on fluorescent labeling. Another approach may utilize or involve magnetic beads. Then detection may be magnetic chip based detection. In another example, individual microdevice can be detected for determining their types and measuring fluorescent levels on each microdevice, recording the correlation information between types of individual microdevice and fluorescent levels on each microdevice.

Detection of individual microdevices may involve the use of instruments such as a microscope, an optical-imager, or a image-capture system. This can be accomplished by methods or devices known in the art such as an image-processing and/or pattern recognition programs.

Sorting such microfabricated microdevices may also be possible. For example, we could use our on-chip based microparticle switch (pumwitch=pumps & switches for microparticle transportation and sorting). For example, the microparticle switches disclosed in the co-pending U.S. patent application Ser. No. 09/678,263 can be used. The on-chip sorting or separation of microdevices (with the binding partners and the moieties) may use the methods disclosed in the co-pending U.S. patent application Ser. No. 09/678,263, which is incorporated by reference in its entirety. In this case, microfabricated microdevices will be separated according to their encoding patterns. Microfabricated encoding microdevices (i.e. microparticles) having the same patterns will be sorted or moved to the same locations on the chip by applying appropriate electrical signals, based on the detected patterns on the microdevices.

The microfabricated, encoding particles (or the microdevices or the microdevices) can be used both on biochip or off biochip. In off-biochip cases, these microfabricated particles (i.e. microdevices) can be used in a manner similar to that of to microbeads in current biological/biomedical applications. The microfbaricated particles (i.e., the microdevices) can be used to separate cells, isolate target molecules, separate molecules, transport cells/molecules, etc. Primarily, the particles (i.e., the microdevices) are used as binding partners for binding to specific moieties or bioanalytes. In on-chip cases, these microfabricated encoding particles (i.e. the microdevices) can be used as binding partners to bind bioanalytes or moieties or other biomolecules. The on-chip use of these microfabricated encoding particle (i.e. the microdevices) or microdevices can be the same as the procedure of manipulating moieties through binding partners as described in the co-pending U.S. patent application Ser. No. 09/636,104, filed Aug. 10, 2000.

3. Library Synthesis Using Information Encoded Sortable Particles

Another specific embodiment is to use microdevices of the present invention for library synthesis. Information Encoded Sortable Particles (IESPs) can be used in library synthesis. This allows vast addressable arrays to be generated for any molecule that can be synthesized using conventional solid phase methods. For simplicity DNA library synthesis has been chosen as an example.

Background

The one-bead/one-compound procedure is well-established and permits the use of existing solid phase chemistry, e.g., peptide and nucleic acid synthesis. The following example will demonstrate the typical method of preparing DNA on beads using the one-bead/one-compound approach. In the case of DNA there are 4 bases, A, T, C, and G. Beads are divided randomly into 4 tubes labeled A, T, C, and G and the corresponding base is chemically coupled to the beads in each tube. The beads from each tube are then mixed together and randomly divided into another set of 4 tubes labeled A, T, C and G and the corresponding base is once again added. This process of dividing, coupling, and mixing is repeated N times, where N is the length of the individual oligonucleotide chains. This process as the name implies produces beads that contain only a single type of compound. Consider a specific example where N is 10 and 10,000,000 beads, at the end of the synthesis, the library will consist of all possible 10-mers (1,048,576 or $4^{10}$) that are represented (on average) 9-10 times in the library. The amount of each compound on the beads is determined by the chemistry on the bead (number of coupling sites) and it is possible to have $10^6$ or more molecules/bead. Using the one-bead/one-compound strategy it is therefore straightforward to generate vast arrays of compounds, but there are major restrictions. The identity of the compound on any particular bead is not known or determinable other than through some type of analysis of the compound on the bead (e.g. sequencing or mass spectrometry). The ability to represent an entire sequence space is limited by the physical constraints imposed by the volume of the beads, i.e., in practice it is difficult to generate or screen bead libraries larger than $\sim 10^{10}$. For example, consider a library of DNA 25-mers, there are over $10^{15}$ 25mers and at least 4 times as many beads would be required to insure that each 25-mer is represented at least once in the final bead library. Even if 1 micron beads were used, the library would still occupy several liters. When the number of beads is less than the number of possible compounds the library no longer represents the entire sequence space. Since all the steps are random, knowledge of the specific sequences contained in the library is lost when the number of compounds exceeds the number of beads.

Information Encoded Sortable Particles (IESPs)

Passive Sorting

If the particles (beads) are encoded then at each step in the synthesis described in the previous section the identity of each bead can be determined and that information stored. At the end of the process, the DNA sequence on each particle will be known to correspond to a specific particle. This means, that in any assay, identifying the code on the particle reveals the identity of the compound on that particle. Such knowledge is essential when carrying out assays leading to thousands or millions of positive responses such as occurs in mRNA profiling (it is impractical to sequence thousands or millions of beads). In addition, because each synthetic step is recorded, the precise representation within the library is known. Consequently, even in libraries where the number of compounds greatly exceeds the number of beads, the identity of every compound within the library is known.

Active Sorting

Sorting can also be active, and in this case instead of particles being mixed and randomly distributed following each synthetic step, specific predetermined particles are instead sorted into specific tubes. In an active sorting procedure the specific sequences are preassigned to individual particles. For example, the IESP assigned the sequence ATCGGGTTAA (SEQ ID NO:1) would go to the A tube in the first step of synthesis then to the T tube in the second, the C tube in the third, etc. Consequently, active sorting could be used to generate a library corresponding to any particular predetermined subset of sequence space. For example, this procedure could be used to generate a library of $10^6$ 50-mers all of which correspond to a sequence in the human genome. This is a very small and specific subset in a sequence space of over $10^{30}$ ($4^{50}$). Active sorting permits the precise determination of the number of times each compound is represented in the collection of particles, making it possible to generate arrays containing only unique representations. Both passive and active sorting procedures, by identifying the particles containing specific compounds, make it possible to create specific sub-arrays of the full compound library without resynthesis, for example, selecting from an IESP library containing all possible DNA 10-mers only those with a G at position 4 but lacking C at positions 2 and 6. The major source of error in the generation of these libraries is likely to be due to mistakes in sorting, i.e., misidentification of a particle during the synthesis. However, since active sorting directs specific particles to specific tubes after each synthesis step, an error would have to occur on the same particle in two consecutive cycles in order to propagate, greatly reducing the frequency of misidentification errors.

Applications

The examples below represent a few of the many possible applications of IESPs. IESPs enable the inexpensive manufacture of vast arrays of known sequence. Apart from ease of synthesis using IESPs there are a number of general advantages to libraries produced on particles as opposed to membranes or glass slides used in competing technologies. Because of the greater freedom in synthesis it is possible to display compounds on the end of soluble spacer molecules allowing for more effective presentation of the library (this can be essential in the case of hydrophobic compounds which may be otherwise insoluble). Additionally, in assays involving target binding, isolation of a particular IESP directly corresponds to purification of its target, raising the possibility of carrying out secondary analyses following the initial capture process. Purification procedures can benefit from the ability of IESPs to be rapidly sorted using a FACS machine to sequester positives followed by a final sorting and identification using a slower IESP sorting device.

DNA Arrays

DNA arrays for determining mRNA levels could be generated using IESPs. Such arrays would be expected to be superior to those of the currently used arrays. Membrane based arrays of synthetic oligonucleotides are severely limited in the length of the oligonucleotides that can be displayed. By contrast, particle based syntheses have no such limitations and oligonucleotide sequences significantly longer than those used by the membrane based arrays can be employed to minimize background, e.g., permit much more stringent hybridization conditions. In addition, the use of longer oligonucleotides results in other advantages. Minor synthesis errors do not affect the result (an error in one or two errors in a 50-mer is inconsequential, in a 25-mer it is fatal). Similarly SNPs in the target DNA will not affect hybridization.

Peptide Arrays

One of the more intriguing applications of IESPs, not achievable using any current technique, is to generate a peptide library that represents an entire genome. Such peptide arrays would permit screening of various enzymes in an attempt to identify physiological substrates such as receptor ligands or kinase substrates. Existing random peptide libraries are more restricted because they do not correspond directly to the genome but instead sample all of sequence space. For example, a peptide array representing each protein in the human genome by a series of 20-residue peptides which overlap by 10 residues would contain ~$10^7$ peptides, the complete sequence space for all 20-residue peptides is ~$10^{26}$ combinations. Moreover, if it were possible to make such huge random arrays an overwhelming amount of the information would be irrelevant to physiological function (in this example there would be $10^{19}$ as many nonphysiological peptides as physiological ones). Even in a random library consisting of all 8-residue peptides, less than 1% of the peptides are encoded in the human genome.

Since IESP-generated peptide arrays are synthetic they can include, in addition to the 20 common amino acids, unnatural, D-amino acids, and peptide mimetics. Such peptide arrays can be used in screens for drug leads as discussed in the next subsection.

Drug Discovery

One major application for IESPs is in drug discovery. Using well-established solid-phase techniques it should be possible to generate arrays of $10^6$ or more particles. Such arrays could be screened against a single drug target using a fluorescence based detection system. Arraying the IESPs in a monolayer would permit fluorescence detection and identification to be carried out simultaneously. Following the initial analysis a new library of $10^6$ or more compounds based upon the first screening could be generated and the assay repeated. With IESP technology 10-100 fold more information could be determined in a few hours. In addition, more restrictive libraries can be rapidly generated based upon the positive results from earlier screenings. The application of such an iterative process would further enhance the huge competitive advantage of IESP technology for drug design.

Information Encoding

IESP can be used to encode information and to rapidly retrieve information from complex systems. For example, any type of synthetic library generated using IESPs could include a specific DNA tag. Following synthesis, the library could be released from the particles and the assay carried out in solution. The library could then be reattached to IESPs by hybridization for identification. This approach permits interaction in solution followed by chip capture, thus making it possible to carry out assays that are difficult or impossible to perform on molecules bound to a surface. While DNA has been used as an example other specific interactions could be used, e.g., aptamer array-peptide interactions. It is important to note that this approach has significant advantages over competing types of capture approaches using membranes. In particular, using IESPs any tagging sequence can be generated. For example, using DNA 20-mers for tagging it is possible to generate $10^8$ tags where each tag differs from every other by 5 or more bases thus eliminating mismatches and cross hybridization between tags and targets. In addition, since the identity of the compound bound to each specific DNA tag is known, the procedure is easily validated (e.g. can determine if any of the DNA tags fail to hybridize in good yield prior to the analysis).

Soluble tagged IESP generated libraries also makes it possible to utilize multiple libraries in a single assay, e.g., a library of antibodies screened against a library of peptides instead of against a single peptide as is done currently. Another advantage of DNA tagging is that an amplification/labeling step can be included prior to decoding to enhance signal strength. This method is particularly useful when using a library to distinguish differences among a large number of different targets, e.g., identifying synthetic antibodies or ligands that uniquely bind to a particular cell type.

4. High Throughput Antibody Screen Antigen Immobilization of Encoded Microdevice Antigen targets can be immobilized on the microdevice covalently or non-covalently. Antigen target can be peptides, proteins, nucleic acids, polysaccharides, chemical molecules or other molecules that can be recognized by an antibody. Immobilized on each microdevice is a unique antigen target, the identity of which is known. In some instances, it may be beneficial to have a mixture of more than one target antigen immobilized on a microdevice. The identities of the components of such antigen mixtures are also known. Protein targets (1 ng-10 μg) can be immobilized onto a chemically modified surface of the microdevices.

Recombinant Antibody Clones Selection

A. Antibody Library Construction

An antibody library is established by recombinant phage display technologies. Briefly, antibody encoding DNA fragments are amplified from mRNA preparation from human peripheral blood lymphocytes, bone marrow cells or spleen cells through reverse transcription PCR. Mouse antibody fragments can be made from MRNA preparation from spleen cells. Alternatively, antibody fragments can be generated by designed total DNA synthesis or semi DNA synthesis. The DNA fragments encoding IgG heavy chain and light chain are inserted into a phagemid vector respectively by recombinant DNA technologies. The phagemid vector contains a gene encoding filamentous phage (fd) gene III product, which is the C terminal of the inserted antibody gene. The resulting vectors containing antibody encoding genes are transformed into an $E.$ $coli.$ strain (for example TG1) and helper phages are infected into the $E.$ $coli.$ cells. Phages that display antibody are collected from the supernatant of the cell culture. Those phage populations serve as starting materials for the antibody screen.

B. High Throughout Screening of Antibodies

The encoded microdevices (up to 1000 different codes) that have been immobilized with antigens are used to screen antibodies. In a test tube, 100 μl of microdevices suspended in PBS buffer was aliquoted. The 100 μl of microdevice solution contains 100 copies of 1000 (from 1 to 1000) different coded microdevices. One or more than one different peptide antigens, e.g., 10, 100 or 1,000 antigens, is immobilized on each kind of microdevice. The microdevice mixture is incubated with 100 μl of phage library ($10^{10}$p.f.u.) produced by above mentioned method. Incubation condition is 2 hr-18 hr at 4° C. This procedure ensures that the antibody displayed on phage binds to its selected targets. After incubation, the microdevice suspension is washed with wash buffer for 5 times to remove non-bound phages. Then, fluorescence labeled anti-M13 coat protein antibody is incubated with the microdevices suspended in 100 μl of PBS buffer at 37° C. for 2 hrs. And then, the microdevices are washed 3 times with wash buffer.

C. Detecting and Sorting Individual Microdevice

The microdevice mixture is suspended in 0.1-1 ml of PBS buffer. The mixture is loaded into a detection biochip for fluorescence detection and barcode sorting. The whole process is performed on the instrument specialized for the detection. According to the fluorescent signals and encoding information on each microdevice, individual microdevice with fluorescence signal is sorted and collected into a micro well on a microtiter plate. Two information are collected by this process: 1) fluorescence signal on the microdevice indicating that specific phage carrying an antibody is bound on the target on chip; and 2) the target on chip is analyzed by the decoding the pattering information of the microdevice. Accordingly, specific antibody for given target is obtained after the sorting.

D. Antibody Characterization

Microdevices positive for antibodies are collected into microtiter plate wells by the sorting process. Phages bound on the microdevices are released by treatment with proteolytic enzymes or low pH. Released phages are reinfected into $E.$ $coli.$ cells. Individual colonies are obtained by plating the infected $E.$ $coli.$ cells onto nutrient agar plate. Individual colony is selected and cultured for antibody production. Antibody producing cells are selected by an ELISA method using specific antigens. Once specific antibody for a given antigen is obtained, it can be used for large-scale production of a specific antibody.

5. Exemplary Fabrication Processes

FIG. 13 shows one example of the fabrication processes for making one type of the encoding particles. The encoding particles described here have three layers, i.e., top layer, bottom layer and/or middle layer with respect to the orientation shown in FIG. 13, with the encoding features located in the middle layer. The top and bottom layers enclosing the middle layer are of materials that can be modified to attach suitable molecules. The steps in FIG. 13 and described below are just examples of the fabrication procedures that could be used for making the encoding particles. Those who are skilled in the art of microfabrication or micromachining can readily adopt different procedures/protocols based on the materials and geometries of the encoding particles to be fabricated.

As shown in FIG. 13, the exemplary process starts with the preparation of a solid substrate. The substrate should be pre-cleaned to make sure that it is suited for the fabrication. An example of the substrate may be silicon wafer used for semiconductor fabrications. The clean substrate will then be deposited or coated with a sacrificial layer. As described later, the sacrificial layer will be removed at the last step of the fabrication by methods such as dissolving, etching, etc. Examples of the sacrificial layer can be metal, e.g., copper, $Si_3N_4$, or other materials. When choosing appropriate materials for the sacrificial layer, it is necessary that the sacrificial layer can be selectively removed without affecting the materials used for making the encoding particles themselves. The sacrificial layer can be of variable thickness, e.g., ~1 micron. The method for depositing such a sacrificial layer can be sputtering, evaporation or other methods of deposition. The methods chosen for deposition depend on factors such as the sacrificial-layer materials, the thickness of the layer, availability of the methods in the fabrication labs, etc.

After forming the sacrificial layer, the bottom layer, i.e., the first layer as shown in step 3 of the FIG. 13, of the encoding particles is then formed or deposited on the sacrificial layer. This layer can be made of different materials such as silicon dioxide, aluminum oxide, plastics, polymers, etc. Preferably, the bottom layer can be readily modified so that molecules of interest can be attached on the bottom layer surfaces. Various methods can be used for forming such a layer. For example, sputtering or evaporation may be used for depositing a silicon dioxide layer. This bottom layer can be of variable thickness, depending on the specific design of the encoding particles. This layer can be as thin as several nanometers, or as thick as many microns or millimeters. For example, we have fabricated the encoding particles having a bottom layer thickness of 50 nm, 0.1 micron, 0.3 micron, 0.5 micron or 1 micron made of silicon dioxide.

After forming the bottom layer, i.e., the first layer as shown in step 3 of the FIG. 13, of the encoding particles, the middle layer, i.e., the second layer as shown in step 4 of the FIG. 13, is then formed or deposited on the bottom layer. This layer may serve various purposes. It may be used for including the encoding features, as in the case shown in FIG. 13. For example, a metal layer (e.g., aluminum) may be used and the metal layer will be patterned using photolithography to make the encoding features such as lines, dots, squares, numbers, etc. This middle layer may comprise suitable materials so that the encoding particles have certain physical properties. For example, this layer may be of magnetic, ferromagnetic, or ferrimagnetic materials so that the encoding particles have magnetic properties. For example, nickel metal or CoTaZr (Cobalt-Tantalum-Zirconium) alloy or other magnetic materials may be used. Various methods may be used for depositing or forming such a layer, depending on factors such as materials to be deposited, thickness of the layer, availability of the methods. Non-limiting examples are evaporation, sputtering, etc. This layer can be of variable thickness, depending on the designs and requirements for the encoding particles. The layer can be as thin as several nanometers or as thick as many microns or many millimeters. For example, we have fabricated the encoding particles with the middle layer thickness of 0.02 micron, 0.05 micron, 0.1 micron, 0.3 micron, 0.5 micron, 1 micron and 3 microns using various materials including aluminum, nickel, CoTaZr, etc.

After forming the middle layer via various deposition methods, the middle layer may then be patterned for producing required encoding features or producing certain geometrical patterns in this middle layer (i.e., the second layer as shown in step 5 of FIG. 13). The encoding features are used for coding each individual particle. The features may include, but not limited to, numbers, letters, symbols, lines, squares, 1-D bar codes, 2-D bar codes. Many commercially available coding patterns can be used (e.g. Two-dimensional codes in "Automatic I.D. News", October 1995). Patterning of the middle layer can be achieved using techniques such as photolithography with photomasks. Such photolithography-based patterning can be done with a number of methods. Those who are skilled in the art of micro-fabrication can readily determine and choose or develop appropriate protocols for patterning this middle layer to produce required encoding geometries/features, based on the required geometrical sizes of the patterns and the materials of the middle layer. For example, we can use chemical etch for patterning a metal layer by first patterning a coated photoresist layer.

After patterning the middle layer (i.e., the second layer as shown in step 5 of FIG. 13), the top layer (i.e. the third layer as shown in step 6 FIG. 13) may then be formed or deposited on the middle layer. This layer can be made of a number of materials such as silicon dioxide, aluminum oxide, plastics, polymers, etc. In some cases, the top layer can be of the same material as those for the bottom layer. But this does not have to be the case. The top layer may be of different materials/compositions from the bottom layer. Preferably, the top layer materials may be readily modified so that molecules of interest can be attached or added onto the top layer surfaces. Various methods can be used for forming such a layer. For example, sputtering or evaporation may be used for depositing a silicon dioxide layer. This top layer can be of variable thickness, depending on the specific designs of the encoding particles. This layer can be as thin as several nanometers, or as thick as many micrometers or millimeters. For example, we have fabricated the encoding particles having a top layer thickness of 50 mn, 0.1 micron, 0.3 micron, 0.5 micron, 1 micron, 1.5 micron and 1.9 micron made of silicon dioxide. In designing and choosing the optically encoding particles with the layered structures similar to those shown in FIG. 13, care should be taken so that the deposited top layer should cover all the surfaces of the middle layer, especially when the middle layer may be metal or other not-inert materials. But this may not always be a strict requirement. For certain applications, exposure of some middle layer materials due to non-covered top layer to some reaction solutions may not be a problem. In such cases, it may not be necessary to ensure that the coverage of the top layer over the middle is complete.

After depositing the top layer by using the appropriate deposition method, the top layer and the bottom layer may then be patterned to produce individually non-connecting encoding particles. If the bottom layer (i.e. the first layer as shown in step 3 of the figure) and the top layer (i.e., the third layer as shown in step 6 of FIG. 13) are of the same materials, the patterning of the top and bottom layer may be performed simultaneously. But this does not have to be the case. The bottom layer and the top layer may be patterned in two separate steps, especially if the top and bottom layers are made of different materials. For example, we have produced certain encoding particles with silicon dioxide on both the top and bottom layer. For those particles, we have used both chemical etch and dry etch methods to pattern both the top and the bottom layers.

After patterning the top and bottom layer, the encoding particles are made but are still attached to the sacrificial layer. Thus, the last step of the fabrication involves the release of the fabricated encoding particles by removing or etching away the sacrificial layer. For example, certain etching solutions (e.g. acid) can be used to etch a metal sacrificial layer to release the encoding particles.

In the above description, we described an exemplary process for making one type of encoding particles. It is important to know that the encoding particles can be of different configurations to the one shown in FIG. 13. For example, the encoding particles in FIG. 13 are discussed as three-layers, but they can be single layer, two-layer, four-layer, or even more layers. Also, there exists quite different fabrication approaches or methods for making such encoding particles. For example, the fabrication methods described for making dielectric micromotors in Journal of Electrostatics (volume 33, pages 159-195, 1994) by Hagedom et al can be used or modified for making the optically encoding particles of the invention.

6. Exemplary Uses of Microdevices

FIGS. 4-12 illustrates use of exemplary microdevices MicroDisks.

Figure 4A:
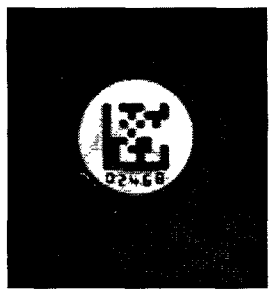
FIG. 4 shows a MicroDisk, an exemplary microdevice of the present invention, containing a 2D Barcode with the numerical representation below.
Figure 4B:
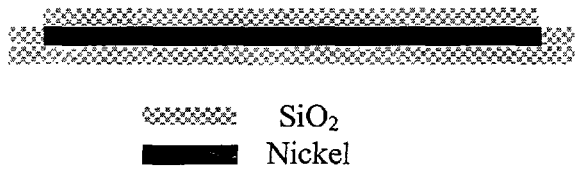

FIG. 4 shows a MicroDisk containing a 2D Bar code with the numerical representation below. MicroDisk is composed of 80µ diameter, 0.5µ thick outer layers of $SiO_2$ with a 70µ diameter 0.5µ thick Nickel central layer (see schematic on left hand side—not drawn to scale). Bright region of encoding pattern is Nickel; dark region consists of $SiO_2$. MicroDisk is illuminated from above. Magnification is 220×.

Figure 5:
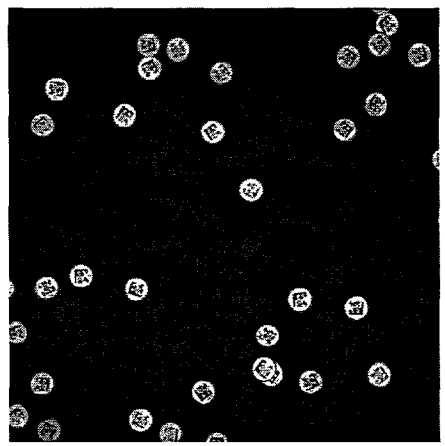
FIG. 5 shows MicroDisks distributed on the surface of a slide.

FIG. 5 shows disks randomly distributed on the surface of a slide. MicroDisks are composed of 80μ diameter, 1.0μ thick outer layers of SiO₂ with a 70μ diameter 0.3μ thick CoTaZr central layer. Magnification is 44×

Figure 6A:
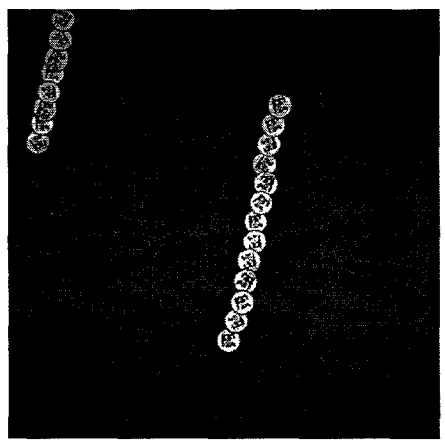
FIG. 6 shows formation of chains caused by presence of a weak magnetic field in the plane (generated by Alnico C-shaped magnet).
Figure 6B:
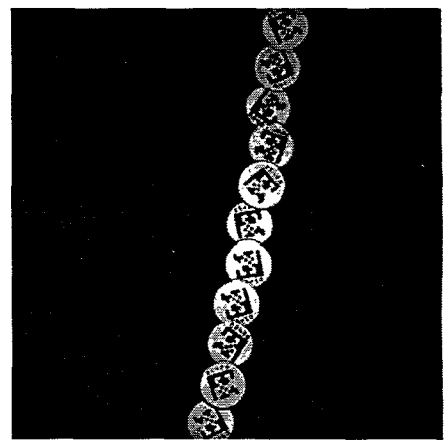

FIG. 6 shows formation of chains caused by presence of weak magnetic field in the plane (generated by Alnico C-shaped magnet). MicroDisks are composed of 80μ diameter, 1.0μ thick outer layers of SiO₂ with a 70μ diameter 0.3μ thick CoTaZr central layer. Left panel: Magnification is 44×; Right panel: Magnification is 88×.

Figure 7:
FIG. 7 shows large number of MicroDisks standing on edge in the presence of a strong magnetic field perpendicular to the plane (generated by Neodymium disk-shaped magnet).

FIG. 7 shows large number MicroDisks standing on edge in the presence of strong magnetic field perpendicular to the plane (generated by Neodymium disk-shaped magnet). MicroDisks are composed of 80μ diameter, 1.9μ thick outer layers of SiO₂ with a 70μ diameter 0.1μ thick CoTaZr central layer. Magnification is 44 ×.

Figure 8A:
FIG. 8 shows 2 MicroDisks.
Figure 8B:
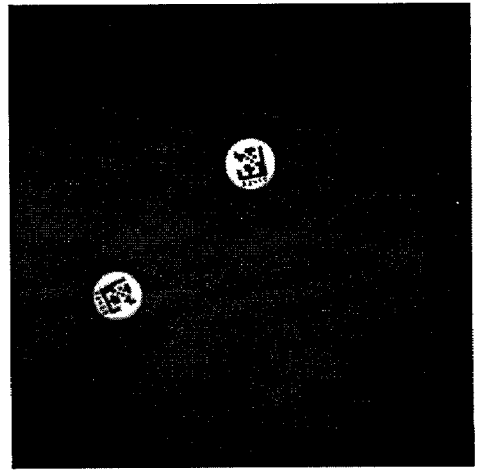

FIG. 8 shows 2 MicroDisks. In left panel they are standing on edge in the presence of a strong magnetic field perpendicular to the plane (generated by Neodymium disk-shaped magnet). Right hand panel shows MicroDisks after magnetic field has been removed. MicroDisks are composed of 80μ diameter, 1.0μ thick outer layers of SiO₂ with a 70μ diameter 0.3μ thick CoTaZr central layer. Magnification is 88×.

FIG. 9 shows orientation of MicroDisks following magnetic manipulation. MicroDisks are composed of 80μ diameter, 1.0μ thick outer layers of SiO₂ with a 70μ diameter 0.3μ thick CoTaZr central layer. Magnification is 88×.

FIG. 10 shows results of covalent attachment experiment. MicroDisks were treated with 3-glycidoxypropyltrimethoxy silane and the resulting epoxide was hydrolyzed with acid to generate a diol surface. Diol-coated MicroDisks were activated with 2,2,2-Trifluoroethanesulfonyl chloride (tresyl chloride). The upper panels show the covalent attachment of a fluorophore (Biocytin-Alexafluor594; Molecular Probes) to the activated MicroDisk. Lower panels show the results of a parallel reaction using non-activated diol-coated MicroDisks. The left-hand panels show bright-field illumination; the right-hand panels show fluorescent signal. After correction for background, the fluorescence signal of the activated MicroDisks is over 100× greater than that of the non-activated diol-coated MicroDisks. MicroDisks are composed of 80μ diameter, 1.0μ thick outer layers of SiO₂ with a 70μ diameter 0.3μ thick CoTaZr central layer. Magnification is 88 ×.

FIG. 11 shows results of bioassay experiment. Mouse IgG was covalently linked to tresyl-activated MicroDisks (upper panel). MicroDisks were then incubated with a fluorescently-labeled anti-mouse antibody (Alexafluor488 goat anti-mouse IgG; Molecular Probes). Lower panels show the results of a parallel reaction using non-activated diol-coated MicroDisks. The left-hand panels show bright-field illumination; the right-hand panels show fluorescent signal. After correction for background, the fluorescence signal of the MicroDisks displaying covalent mouse IgG is over 100× greater than that of the non-activated diol-coated MicroDisks. MicroDisks are composed of 80μ diameter, 1.0μ thick outer layers of SiO₂ with a 70μ diameter 0.3μ thick CoTaZr central layer. Magnification is 88 ×.

FIG. 12 shows further results of bioassay experiment determining the amount of fluorescence signal from both types of MicroDisks in the same measurement. The left-hand panels show bright-field illumination; the right-hand panel shows fluorescent signal. Within each panel MicroDisks containing covalently linked mouse IgG are on the left side and diol-coated MicroDisks are on the right side. Magnification is 88×.

The above examples are included for illustrative purposes only and are not intended to limit the scope of the invention. Many variations to those described above are possible. Examples of these variations include, but not limited to, the substrate materials for making the chips, the electrode structures for generating electric fields, the structure of electromagnetic units for producing magnetic fields, the structures of piezoelectric elements for producing acoustic fields, the structures of optical elements for generating optical fields, the structures of heating/cooling elements for generating temperature gradient, etc. Since modifications and variations to the examples described above will be apparent to those of skill in this art, it is intended that this invention be limited only by the scope of the appended claims.

The invention claimed is:

1. A microdevice, which microdevice comprises:
   a) a substrate;
   b) a photorecognizable coding pattern on said substrate; and
   c) a binding partner on a surface of the microdevice that is capable of binding to a moiety to be manipulated,
   wherein said photorecognizable coding pattern comprises a hole not penetrating through the entire depth of said substrate,
   and said microdevice has dimensions from about 1 to about 500 microns, and does not comprise an anodized metal surface layer;
   wherein the substrate comprises a silicon layer and a metal layer;
   and the metal layer comprises a patterned magnetic material.

2. The microdevice of claim 1, wherein the magnetic material comprises nickel.

3. The microdevice of claim 1, wherein the magnetic material comprises CoTaZr alloy.

4. The microdevice of claim 1, wherein the patterned magnetic material is an encoding feature.

5. The microdevice of claim 1, wherein the substrate comprises a silicon layer and a metal layer, and said silicon is silicon dioxide or silicon nitride.

6. The microdevice of claim 1, wherein the photorecognizable coding pattern is in an encoding layer, and the metal layer comprising a patterned magnetic material is a different layer.

7. The microdevice of claim 5, wherein the metal layer comprises a magnetic alloy.

8. The microdevice of claim 5, wherein the metal layer comprises nickel metal or CoTaZr (Cobalt-Tantalum-Zirconium) alloy.

9. The microdevice of claim 5, wherein the silicon is silicon dioxide.

10. The microdevice of claim 5, wherein the thickness of the substrate is from about 1 micron to about 10 microns.

11. The microdevice of claim 9, wherein the substrate is a rectangle having a surface area from about 10 squared-microns to about 10,000 squared-microns.

12. A microdevice, which microdevice comprises:
   a) a substrate;
   b) a photorecognizable coding pattern on said substrate; and
   c) a binding partner that is capable of binding to a moiety to be manipulated, wherein the binding partner is coated on a surface of the microdevice;
   wherein said photorecognizable coding pattern comprises a hole not penetrating through the entire depth of said substrate,
   and wherein said binding partner comprises a cell, a cellular organelle, a virus, or an antibody, and said microdevice has dimensions from about 1 to about 500 microns, and does not comprise an anodized metal surface layer;
wherein the substrate comprises a silicon layer and a metal layer
wherein the metal layer comprises nickel metal or CoTaZr (Cobalt-Tantalum-Zirconium) alloy.

13. The microdevice of claim 12, further comprising a detectable marker or a molecular tag.

14. The microdevice of claim 13, wherein the detectable marker is a dye, a radioactive substance or a fluorescent substance.

15. A kit for manipulating a moiety, which kit comprises:
a) the microdevice of claim 12, and
b) a chip on which the microdevice can be manipulated when the microdevice is coupled to a moiety to be manipulated.

16. An array for detecting moieties, which array comprises a plurality of microdevices placed or immobilized on a surface, wherein each of said microdevices is a microdevice of claim 12.

17. The microdevice of claim 12, wherein the thickness of the substrate is from about 1 to about 200 microns.

18. The microdevice of claim 12, wherein the thickness of the substrate is from about 1 to about 50 microns.

19. The microdevice of claim 1, which comprises a plurality of encoding layers.

20. The microdevice of claim 19, wherein the metal layer comprising a patterned magnetic material comprises one encoding layer, and the photorecognizable encoding pattern is comprised in another encoding layer.

21. The microdevice of claim 1, further comprising an orientation marker.

22. The microdevice of claim 19, further comprising an orientation marker.

23. The microdevice of claim 1, wherein the metal layer is a magnetic film.

24. The microdevice of claim 12, wherein the metal layer is a magnetic film.

* * * * *